(12) United States Patent
Miyoshi et al.

(10) Patent No.: US 8,435,741 B2
(45) Date of Patent: May 7, 2013

(54) ISOTHERMAL NUCLEIC ACID AMPLIFICATION METHOD USING SURFACTANT

(75) Inventors: Hayato Miyoshi, Kanagawa (JP); Yoshihide Iwaki, Kanagawa (JP); Toshihiro Mori, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 505 days.

(21) Appl. No.: 12/179,098

(22) Filed: Jul. 24, 2008

(65) Prior Publication Data

US 2009/0170096 A1 Jul. 2, 2009

(30) Foreign Application Priority Data

Jul. 26, 2007 (JP) ................................ 2007-194273
Apr. 28, 2008 (JP) ................................ 2008-117510

(51) Int. Cl.
*C12Q 1/68* (2006.01)
*C12P 19/34* (2006.01)

(52) U.S. Cl.
USPC ....................................... 435/6.12; 435/91.2

(58) Field of Classification Search ........................ None
See application file for complete search history.

(56) References Cited

U.S. PATENT DOCUMENTS

| | | | | |
|---|---|---|---|---|
| 2003/0186234 | A1 | 10/2003 | Kurn | |
| 2006/0252058 | A1* | 11/2006 | Hayashi et al. | 435/6 |
| 2010/0047794 | A1* | 2/2010 | Miyoshi et al. | 435/6 |

FOREIGN PATENT DOCUMENTS

| | | |
|---|---|---|
| CN | 101003836 A | 7/2007 |
| EP | 1306448 A2 | 5/2003 |
| EP | 1837408 A1 | 9/2007 |
| JP | 5-130870 A | 5/1993 |
| JP | 2002-233379 A | 8/2002 |
| JP | 2004-154008 A | 6/2004 |
| JP | 2004-257901 A | 9/2004 |
| WO | WO-2005/070027 A2 | 8/2005 |

OTHER PUBLICATIONS

Poon et al., Sensitive and Inexpensive Molecular Test for Falciparum Malaria: Detecting *Plasmodium falciparum* DNA Directly from Heat-Treated Blood by Loop-Mediated Isothermal Amplification, Clinical Chemistry 52, No. 2 pp. 303-306, published online Dec. 8, 2005.*

Poon et al., Supplemental Fig. 1, Sensitive and Inexpensive Molecular Test for Falciparum Malaria: Detecting *Plasmodium falciparum* DNA Directly from Heat-Treated Blood by Loop-Mediated Isothermal Amplification, Clinical Chemistry 52, No. 2 pp. 303-306, published online Dec. 8, 2005.*

ChemBink, TWEEN 20 (polyoxyethylene sorbitan monolaurate), 2010, pp. 1-2.*
HBL Systems, TWEEN 20 (polyoxyethylene sorbitan monolaurate), 2010, pp. 1-4.*
Thai et al., Development and Evaluation of a Novel Loop-Mediated Isothermal Amplification Method for Rapid Detection of Severe Acute Respiratory Syndrome Coronavirus, Journal of Clinical Microbiology, vol. 42, No. 5, May 2004, p. 1956-1961.*
Mitani et al., Rapid SNP diagnostics using asymmetric isothermal amplification and a new mismatchsuppression technology, Nature Methods, vol. 4 No. 3, Mar. 2007, pp. 257-262 and also Published Online Feb. 18, 2007.*
Notomi et al., "Loop-Mediated Isothermal Amplification of DNA", Nucleic Acids Research, vol. 28, No. 12, pp. i-vii, (2000), XP-002292090.
Mitani et al., "Rapid SNP Diagnostics Using Asymmetric Isothermal Amplification and a New Mismatch-Suppression Technology", Nature Methods, vol. 4, No. 3, pp. 257-262, (Mar. 2007), XP009084707.
Wang et al., "Homogeneous Real-Time Detection of Single-Nucleotide Polymorphisms by Strand Displacement Amplification on BD Probetec ET System", Clinical Chemistry, vol. 49, No. 10, pp. 1599-1607, (2003), XP-002435887.
Andrew Fire et al.: Rolling replication of short DNA circles: Proc. Natl. Acad. Sci. vol. 92: pp. 4641-4645: May 1995.
Bio Industry, vol. 18. No. 2, 2001 with English translation.
Chiyoji Abe et al.; Detection of *Mycobacterium tuberculosis* in Clinical Specimens. : Journal of Clinical Microbiology, vol. 31: No. 12; pp. 3270-03274. Dec. 1993.
J. Compton: Nucleic acid sequence-based amplification; Nature; 350: pp. 91-92: 1991.
Chinese Office Action, dated May 3, 2012, for Chinese Application No. 200810133285.0, including English translation.
European Office Action, dated May 24, 2012, for European Application No. 08013478.6.
Hafner et al., "Isothermal Amplification and Multimerization of DNA by Bst DNA Polymerase," BioTechniques, vol. 30, No. 4, Apr. 2001, XP008011191, pp. 852-867 (not all pages provided).

* cited by examiner

*Primary Examiner* — Kenneth R. Horlick
*Assistant Examiner* — David Thomas
(74) *Attorney, Agent, or Firm* — Birch, Stewart, Kolasch & Birch, LLP

(57) ABSTRACT

An object to be achieved by the present invention is to provide a nucleic acid amplification method by which a nucleic acid can be amplified substantially isothermally using oligonucleotide primers and DNA polymerase capable of strand displacement. The present invention provides a nucleic acid amplification method which comprises performing substantially isothermal incubation of a reaction solution containing at least one type of deoxynucleotide triphosphate, at least one type of DNA polymerase having strand displacement activity, a divalent cation, at least 0.01% or more surfactant, at least two types of oligonucleotide primer, and the nucleic acid fragment as a template so as to perform a polymerase reaction that initiates from the 3' end of the primer and thus amplifying the nucleic acid fragment.

28 Claims, 19 Drawing Sheets

Example 1 Level 1

"No Ct" indicates that no amplification took place.

Example 1 Level 2

"No Ct" indicates that no amplification took place.

Example 1 Level 3

|  | Ct value (min) |
|---|---|
| Nucleic acid (+) | 2 4. 3 |
|  | 2 4. 1 |
|  | 2 3. 7 |
|  | 2 5. 3 |
| Nucleic acid (−) | N o C t |
|  | N o C t |
|  | N o C t |
|  | N o C t |

"No Ct" indicates that no amplification took place.

Example 1 Level 4

|  | Ct value (min) |
|---|---|
| Nucleic acid (+) | 1 9. 3 |
|  | 2 2. 3 |
|  | 1 9. 3 |
|  | 2 0. 8 |
| Nucleic acid (−) | 3 2. 3 |
|  | 2 4. 9 |
|  | 2 6. 9 |
|  | 2 2. 7 |

"No Ct" indicates that no amplification took place.

Fig. 5

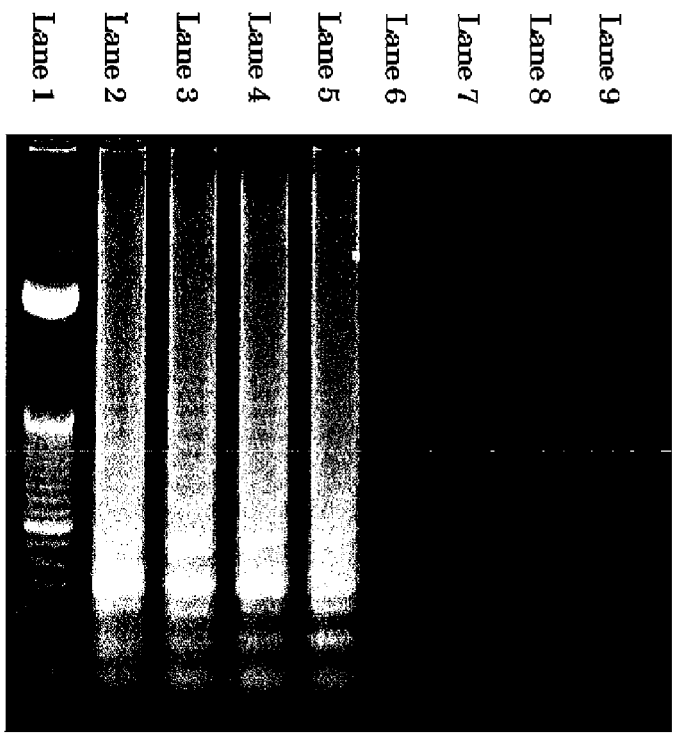

Lane 1 : 50bp ladder (Invitrogen)
Lane 2 : Amplified product of Example 1 at Level 1 (Nucleic acid (+))
Lane 3 : Amplified product of Example 1 at Level 1 (Nucleic acid (+))
Lane 4 : Amplified product of Example 1 at Level 1 (Nucleic acid (+))
Lane 5 : Amplified product of Example 1 at Level 1 (Nucleic acid (+))
Lane 6 : Amplified product of Example 1 at Level 1 (Nucleic acid (-))
Lane 7 : Amplified product of Example 1 at Level 1 (Nucleic acid (-))
Lane 8 : Amplified product of Example 1 at Level 1 (Nucleic acid (-))
Lane 9 : Amplified product of Example 1 at Level 1 (Nucleic acid (-))

Fig. 6

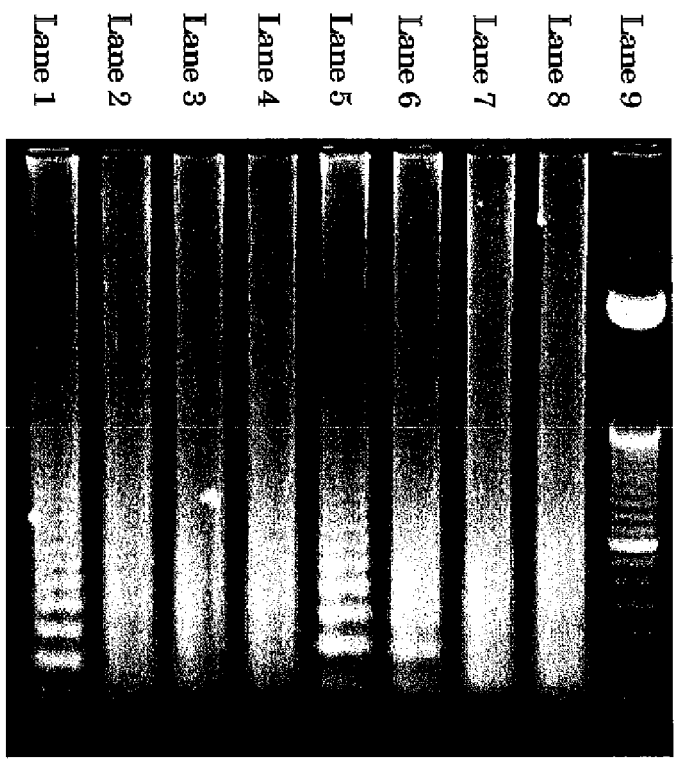

Lane 1 : Amplified product of Example 1 at Level 2 (Nucleic acid (+))
Lane 2 : Amplified product of Example 1 at Level 2 (Nucleic acid (+))
Lane 3 : Amplified product of Example 1 at Level 2 (Nucleic acid (+))
Lane 4 : Amplified product of Example 1 at Level 2 (Nucleic acid (+))
Lane 5 : Amplified product of Example 1 at Level 2 (Nucleic acid (-))
Lane 6 : Amplified product of Example 1 at Level 2 (Nucleic acid (-))
Lane 7 : Amplified product of Example 1 at Level 2 (Nucleic acid (-))
Lane 8 : Amplified product of Example 1 at Level 2 (Nucleic acid (-))
Lane 9 : 50bp ladder (Invitrogen)

Example 2  Level 1

"No Ct" indicates that no amplification took place.

Example 2  Level 2

"No Ct" indicates that no amplification took place.

Example 2 Level 3

|  | Ct value (min) |
|---|---|
| Nucleic acid (+) | 2 4. 3 |
|  | 2 3. 5 |
|  | 2 5. 4 |
| Nucleic acid (−) | N o C t |
|  | N o C t |
|  | N o C t |

"No Ct" indicates that no amplification took place.

Example 2 Level 4

|  | Ct value (min) |
|---|---|
| Nucleic acid (+) | 2 4. 5 |
|  | 2 3. 9 |
|  | 2 4. 4 |
| Nucleic acid (−) | N o C t |
|  | N o C t |
|  | N o C t |

"No Ct" indicates that no amplification took place.

Example 3 Level 1

"No Ct" indicates that no amplification took place

Example 3 Level 2

"No Ct" indicates that no amplification took place

Example 3 Level 3

|  | Ct value (min) |
|---|---|
| Nucleic acid (+) | 2 7. 9 |
|  | 2 9. 1 |
|  | 2 9. 4 |
| Nucleic acid (−) | N o C t |
|  | N o C t |
|  | N o C t |

"No Ct" indicates that no amplification took place

Example 3 Level 4

|  | Ct value (min) |
|---|---|
| Nucleic acid (+) | 2 4. 6 |
|  | 2 7. 7 |
|  | 2 5. 5 |
| Nucleic acid (−) | N o C t |
|  | N o C t |
|  | N o C t |

"No Ct" indicates that no amplification took place

Example 3 Level 5

|  | Ct value(min) |
|---|---|
| Nucleic acid (+) | 27.0 |
|  | 26.1 |
|  | 26.8 |
| Nucleic acid (−) | No Ct |
|  | No Ct |
|  | No Ct |

"No Ct" indicates that no amplification took place

Example 3 Level 6

|  | Ct value(min) |
|---|---|
| Nucleic acid (+) | 25.1 |
|  | 25.6 |
|  | 25.8 |
| Nucleic acid (−) | No Ct |
|  | No Ct |
|  | No Ct |

"No Ct" indicates that no amplification took place

Example 3 Level 7

| | Ct value(min) |
|---|---|
| Nucleic acid (+) | 27.6 |
| | 26.6 |
| | 27.1 |
| Nucleic acid (−) | No Ct |
| | No Ct |
| | No Ct |

"No Ct" indicates that no amplification took place

Example 3 Level 8

| | Ct value(min) |
|---|---|
| Nucleic acid (+) | 24.9 |
| | 23.9 |
| | 25.2 |
| Nucleic acid (−) | 40.8 |
| | 34.3 |
| | 47.9 |

"No Ct" indicates that no amplification took place

Example 3 Level 9

"No Ct" indicates that no amplification took place

Example 4 Level 1

"No Ct" indicates that no amplification took place

Example 4 Level 2

| | Ct value(min) |
|---|---|
| | 24.9 |
| Nucleic acid (+) | 23.6 |
| | 23.7 |
| | 52.2 |
| Nucleic acid (−) | 58.1 |
| | 59.1 |

"No Ct" indicates that no amplification took place

Example 4 Level 3

| | Ct value(min) |
|---|---|
| | 20.1 |
| Nucleic acid (+) | 24.8 |
| | 24.5 |
| | 58.1 |
| Nucleic acid (−) | 50.2 |
| | No Ct |

"No Ct" indicates that no amplification took place

Example 4 Level 4

"No Ct" indicates that no amplification took place

Example 4 Level 5

"No Ct" indicates that no amplification took place

Example 4  Level 6

"No Ct" indicates that no amplification took place

Example 4  Level 7

"No Ct" indicates that no amplification took place

Example 4  Level 8

|  | Ct value (min) |
|---|---|
| Nucleic acid (+) | 23.0 |
|  | 22.3 |
|  | 23.9 |
| Nucleic acid (−) | 28.1 |
|  | 43.4 |
|  | 50.8 |

"No Ct" indicates that no amplification took place

Example 4  Level 9

|  | Ct value (min) |
|---|---|
| Nucleic acid (+) | 25.7 |
|  | 22.5 |
|  | 22.4 |
| Nucleic acid (−) | 42.1 |
|  | 38.5 |
|  | 40.5 |

"No Ct" indicates that no amplification took place

Example 5 Level 1

|  | Ct value (min) |
|---|---|
| Nucleic acid (+) | 18.5 |
|  | 21.1 |
| Nucleic acid (−) | 38.2 |
|  | 58.3 |

"No Ct" indicates that no amplification took place.

Example 5 Level 2

|  | Ct value (min) |
|---|---|
| Nucleic acid (+) | 21.4 |
|  | 22.0 |
| Nucleic acid (−) | No Ct |
|  | No Ct |

"No Ct" indicates that no amplification took place.

Example 6

Example 7

"No Ct" indicates that no amplification took place

Example 8

|  | Ct value (min) |
|---|---|
| Nucleic acid (+) | 2 6. 6 |
|  | 2 5. 4 |
|  | 2 5. 9 |
|  | 2 4. 8 |
| Nucleic acid (−) | No Ct |
|  | No Ct |
|  | No Ct |
|  | No Ct |

"No Ct" indicates that no amplification took place

Example 9

|  | Ct value (min) |
|---|---|
| Nucleic acid (+) | 2 3. 9 |
|  | 2 4. 9 |
|  | 2 3. 5 |
|  | 2 1. 4 |
| Nucleic acid (−) | No Ct |
|  | No Ct |
|  | No Ct |
|  | No Ct |

"No Ct" indicates that no amplification took place

ISOTHERMAL NUCLEIC ACID AMPLIFICATION METHOD USING SURFACTANT

TECHNICAL FIELD

The present invention relates to a nucleic acid amplification method. More specifically, the present invention relates to a nucleic acid amplification method that comprises performing a polymerase reaction through substantially isothermal incubation of a reaction solution using DNA polymerase capable of strand displacement.

BACKGROUND ART

In molecular biological research, nucleic acid amplification is generally performed by an enzymatic method using DNA polymerase. Polymerase chain reaction (PCR) is broadly known as a nucleic acid amplification method. For amplification of a target nucleic acid sequence, the PCR method comprises the three steps of: denaturing (denaturation step) double-stranded DNA as a template into single-stranded DNAs; annealing (annealing step) primers to the single-stranded DNAs; and elongating (elongation step) complementary strands using the primers as origins. According to a general PCR method, the denaturation step, the annealing step, and the elongation step are each performed at different temperatures using a thermal cycler. However, implementation of nucleic acid amplification reactions at three different types of temperature is problematic in that temperature control is complicated and time loss increases in proportion to the number of cycles.

Hence, nucleic acid amplification methods that can be performed under isothermal conditions have been developed. Examples of such methods include An SDA method (Strand Displacement Amplification: JP Patent Publication (Kokai) No. 5-130870 A (1993)), RCA (Rolling Circle Amplification: Proc. Natl. Acad. Sci, vol. 92, 4641-4645 (1995)), ICAN (Isothermal and Chimeric primer-initiated Amplification of Nucleic acids), LAMP (Loop-Mediated Isothermal Amplification of DNA; Bio Industry, vol. 18, No. 2 (2001)), NASBA (Nucleic acid Sequence-based Amplification method; Nature, 350, 91-(1991)), and TMA (Transcription mediated amplification method; J. Clin Microbiol. Vol. 31, 3270- (1993)).

An SDA method (JP Patent Publication (Kokai) No. 5-130870 A (1993)) is a cycling assay method using exonuclease, which is a method for amplifying a target site of a target nucleic acid fragment using a polymerase elongation reaction. This method comprises performing a polymerase elongation reaction using primers (as origins) that have specifically hybridized to target sites of target nucleic acid fragments, while causing 5'→3' exonuclease to act thereon, so as to degrade the primers from the opposite directions. New primers undergo hybridization instead of the degraded primers, so that another elongation reaction proceeds again with the use of DNA polymerase. Such an elongation reaction with the use of polymerase and such a degradation reaction with the use of exonuclease by which the strand that has been elongated is removed are repeated periodically in order. Here, the elongation reaction with the use of polymerase and the degradation reaction with the use of exonuclease can be implemented under isothermal conditions. However, the use of exonuclease in addition to polymerase is required, and thus the method is expensive and the design of primers should be improved.

A LAMP method is a method for amplifying target sites of a target nucleic acid fragment that has been developed in recent years. This method is a method for amplifying target sites of a target nucleic acid fragment as special structure which is complementary to the elongated region from the 3' terminal by 5' terminal of the primer, under isothermal conditions through the use of at least four types of primer that complementarily recognize at least six specific sites of a target nucleic acid fragment and strand-displacement-type Bst DNA polymerase lacking 5'→3' nuclease activity and catalyzing an elongation reaction while liberating double-stranded DNA on the template in the form of single-stranded DNAs. However, the method requires the use of at least four types of primer that recognize six specific sites, so that the design of primers is very difficult.

An ICAN method is a method for amplifying target sites of a target nucleic acid fragment that has been developed in recent years. The ICAN method is an isothermal gene amplification method using RNA-DNA chimeric primers, DNA polymerase having strand displacement activity and template exchange activity, and RNaseH. After chimeric primers bind to a template, a complementary strand is synthesized by DNA polymerase. Subsequently, RNaseH cleaves RNA portions derived from the chimeric primers and then an elongation reaction accompanied by a strand displacement reaction and a template exchange reaction takes place repeatedly from the cleaved sites, so that the gene amplification is performed. However, this method also requires the use of special primers that are chimeric primers and thus the design of such primers is very difficult.

JP Patent Publication (Kohyo) No. 11-509406 A discloses an amplification method, by which, in the presence of DNA polymerase capable of strand displacement, DNA within a target region is amplified by an isothermal reaction using at least a set of oligonucleotide primers. However, the method disclosed in JP Patent Publication (Kohyo) No. 11-509406 A is problematic in that it requires a relatively long reaction time, for example. Therefore, it has been desired to develop a nucleic acid amplification method that can be conveniently implemented isothermally via simple primer design, as with the PCR method.

DISCLOSURE OF THE INVENTION

An object to be achieved by the present invention is to provide a nucleic acid amplification method by which a nucleic acid can be amplified substantially isothermally using oligonucleotide primers and DNA polymerase capable of strand displacement. Furthermore, an object to be achieved by the present invention is to provide a nucleic acid amplification method by which a target nucleic acid sequence can be amplified in a short time and a target nucleic acid sequence can be specifically amplified. Furthermore, an object to be achieved by the present invention is to provide a nucleic acid amplification method with a simpler primer design.

As a result of intensive studies to achieve the above objects, the present inventors have discovered that a nucleic acid fragment can be efficiently amplified within a short time when a polymerase reaction that is initiated from the 3' end of a primer is performed through substantially isothermal incubation of a reaction solution containing deoxynucleotide triphosphate, DNA polymerase capable of strand displacement, a divalent cation, a surfactant, oligonucleotide primers, and a nucleic acid fragment as a template. Thus, the present inventors have completed the present invention. The oligonucleotide primer used in the present invention is characterized in that it has no complicated structures such as those used in the conventional isothermal amplification methods. For example, it is not necessary that the oligonucleotide primer has a structure which forms a chimera structure which is used in the ICAN method or a loop structure which is used in the LAMP method.

Specifically, the present invention provides a nucleic acid amplification method which comprises performing substantially isothermal incubation of a reaction solution containing at least one type of deoxynucleotide triphosphate, at least one type of DNA polymerase having strand displacement activity, a divalent cation, at least 0.01% or more surfactant, at least two types of oligonucleotide primer, and the nucleic acid fragment as a template so as to perform a polymerase reaction that initiates from the 3' end of the primer and thus amplifying the nucleic acid fragment.

Preferably, the reaction solution contains at least 0.05% or more surfactant.

Preferably, the surfactant is a nonionic surfactant.

Preferably, the HLB value of the nonionic surfactant is 12 or more.

Preferably, the HLB value of the nonionic surfactant is 14 or more.

Preferably, the nonionic surfactant is selected from among a polyoxyethylene sorbitan fatty acid ester-based surfactant, and a polyoxyethylene alkyl ether-based surfactant.

Preferably, the polyoxyethylene sorbitan fatty acid ester-based nonionic surfactant is polyoxyethylene sorbitan mono fatty acid ester.

Preferably, the polyoxyethylene sorbitan mono fatty acid ester is represented by the following formula:

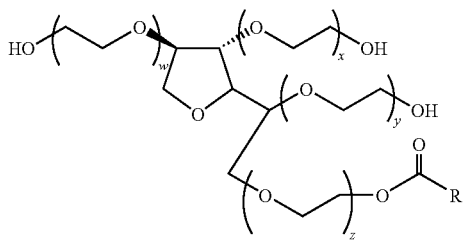

wherein x+y+z+w=20, R is an alkyl group having a carbon number of 12 to 18.

Preferably, the polyoxyethylene sorbitan fatty acid ester-based nonionic surfactant is at least one which is selected from polyoxyethylene(20) sorbitan monolaurate, polyoxyethylene(20) sorbitan monopalmitate, polyoxyethylene(20) sorbitan monostearate, and polyoxyethylene(20) sorbitan monooleate.

Preferably, the reaction solution further contains a melting temperature adjusting agent.

Preferably, the melting temperature adjusting agent is dimethyl sulfoxide, betaine, formamide, or glycerol, or a mixture of two or more types thereof.

Preferably, a reaction solution contains each deoxynucleotide triphosphate of 1.0 mM to 3.0 mM.

Preferably, the reaction solution contains 1 µM to 50 µM olignucleotide primer.

Preferably, the oligonucleotide primers are substantially complementary to portions of the template nucleic acid fragment.

Preferably, only the 3' terminal region of the oligonucleotide primers is substantially complementary to portions of the template nucleic acid fragment.

Preferably, the oligonucleotide primers are substantially complementary to only consecutive 1 site of the template nucleic acid fragment Preferably, the regions on the template, to which the two types of oligonucleotide primers are annealed, are positioned in regions within 1000 bp on the template.

Preferably, at least one type of the polymerase having strand displacement activity is polymerase selected from the group consisting of *Bacillus stearothermophilus*-derived 5'→3' exonuclease-deficient Bst. DNA polymerase, *Bacillus caldotenax*-derived 5'→3' exonuclease-deficient Bca DNA polymerase, and *Thermococcus litoralis*-derived 5'→3' exonuclease-deficient Vent. DNA polymerase.

Preferably, the reaction solution is incubated substantially isothermally at a temperature of 50° C. to 100° C.

Preferably, the time for the substantially isothermal incubation of the reaction solution is within 60 minutes.

Preferably, one or more types of additional oligonucleotide primers, in addition to the aforementioned at least two types of primers, are further added to the reaction solution, so as to perform the reaction.

Preferably, the regions on the template, to which the two types of oligonucleotide primers and the one or more types of additional oligonucleotide primers are annealed, are positioned in regions within 1000 bp on the template.

Further, the present invention provides a method for detecting the presence or the absence of a mutation in a target nucleic acid sequence, which comprises performing the above nucleic acid amplification method of the present invention.

The method for detecting the presence or the absence of a mutation in a target nucleic acid sequence preferably comprises the following steps of:

(1) substantially isothermally incubating a reaction solution containing at least one type of deoxynucleotide triphosphate, at least one type of DNA polymerase having strand displacement activity, a divalent cation, at least one type of nonionic surfactant, at least two types of oligonucleotide primer containing a mutation site, and a nucleic acid fragment containing a target nucleic acid sequence as a template; and (2) determining the presence or the absence of a mutation based on whether or not a nucleic acid amplification reaction takes place by a polymerase reaction that is initiated from the 3' end of the primer.

Preferably, the nonionic surfactant is selected from among a polyoxyethylene sorbitan fatty acid ester-based surfactant, and a polyoxyethylene alkyl ether-based surfactant.

Preferably, the HLB value of the nonionic surfactant is 12 or more.

Preferably, the HLB value of the nonionic surfactant is 14 or more.

According to the present invention, a target nucleic acid sequence can be amplified substantially isothermally. Moreover, according to the present invention, a target nucleic acid sequence can be amplified specifically within a short time.

BRIEF DESCRIPTION OF DRAWINGS

FIG. 5 shows the results of electrophoresis of amplified products of Level 1 (Primer (1) and Primer (2), surfactant (+)) in Example 1.

FIG. 6 shows the results of electrophoresis of amplified products of Level 2 (Primer (1) and Primer (2), surfactant (−)) in Example 1.

PREFERRED EMBODIMENTS OF THE INVENTION

Figure 1:
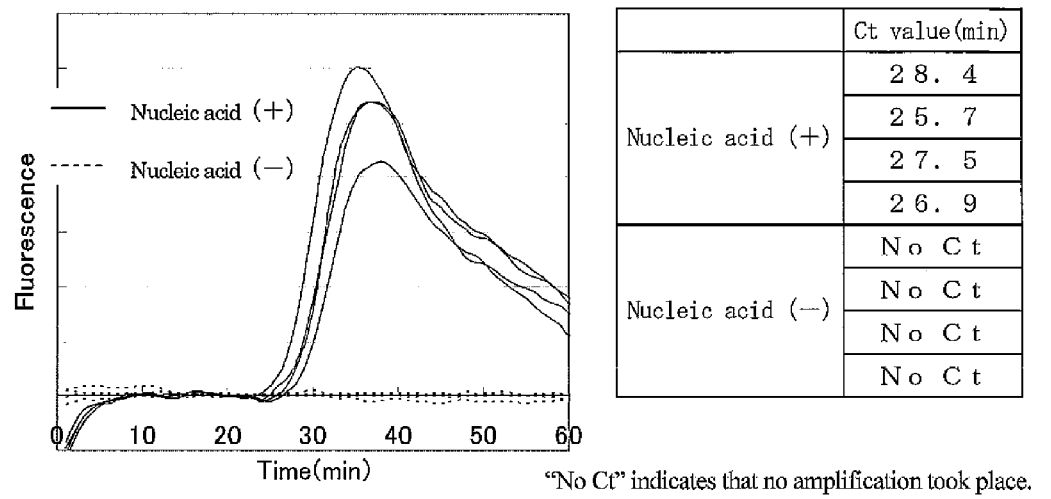
FIG. 1 shows the results of detecting amplified products of Level 1 (Primer (1) and Primer (2), surfactant (+)) in Example 1.
Figure 2:
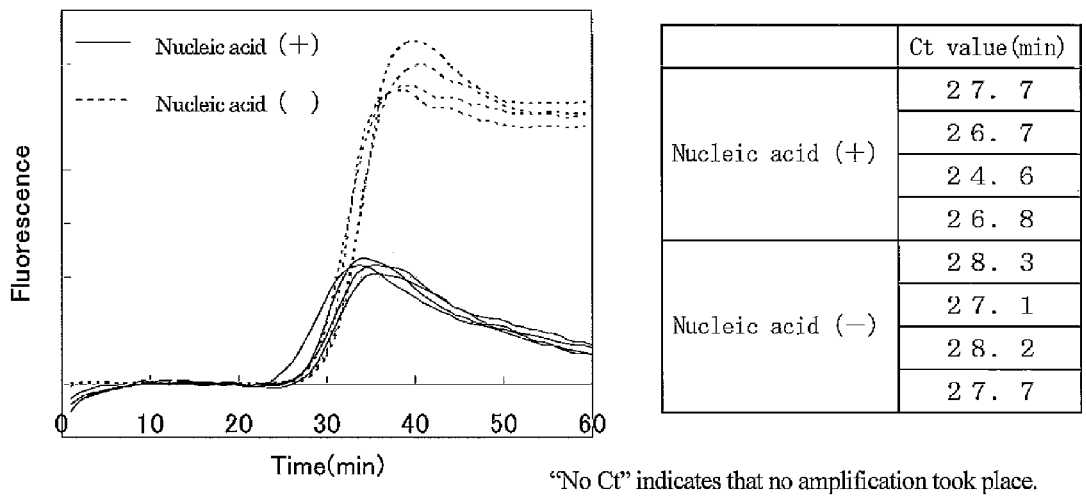
FIG. 2 shows the results of detecting amplified products of Level 2 (Primer (1) and Primer (2), surfactant (−)) in Example 1.
Figure 3:
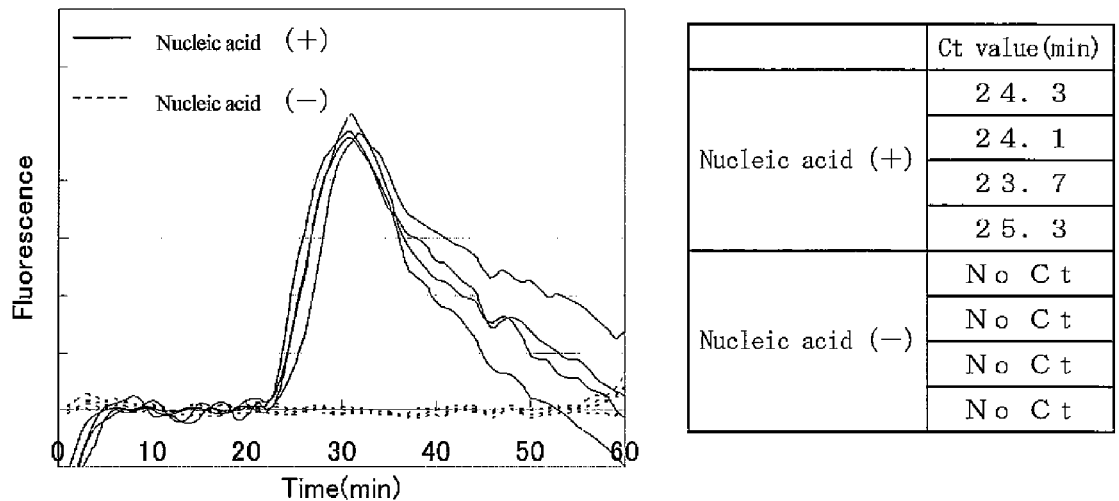
FIG. 3 shows the results of detecting amplified products of Level 3 (Primer (3) and Primer (4), surfactant (+)) in Example 1.
Figure 4:
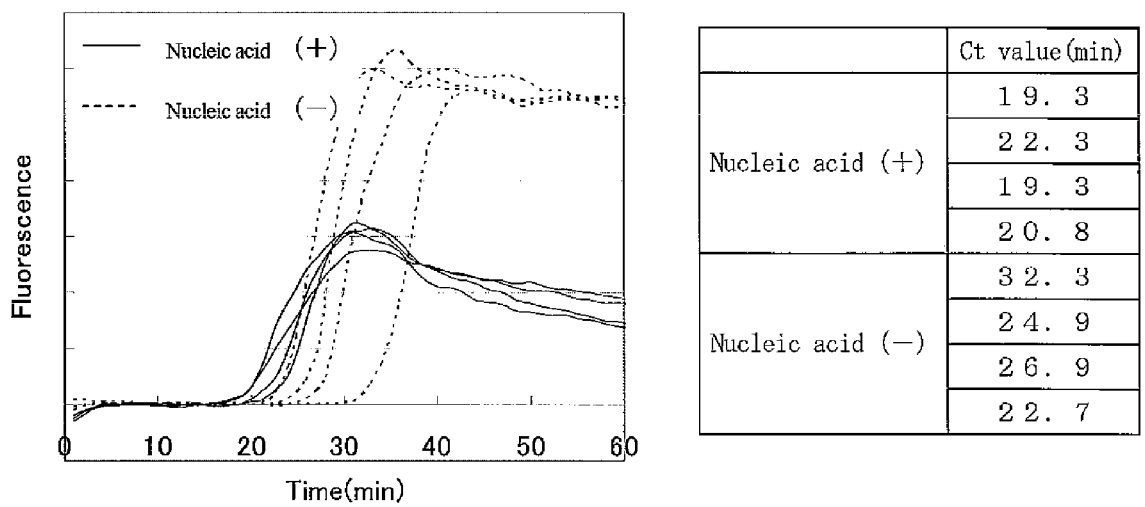
FIG. 4 shows the results of detecting amplified products of Level 4 (Primer (3) and Primer (4), surfactant (−)) in Example 1.
Figure 7:
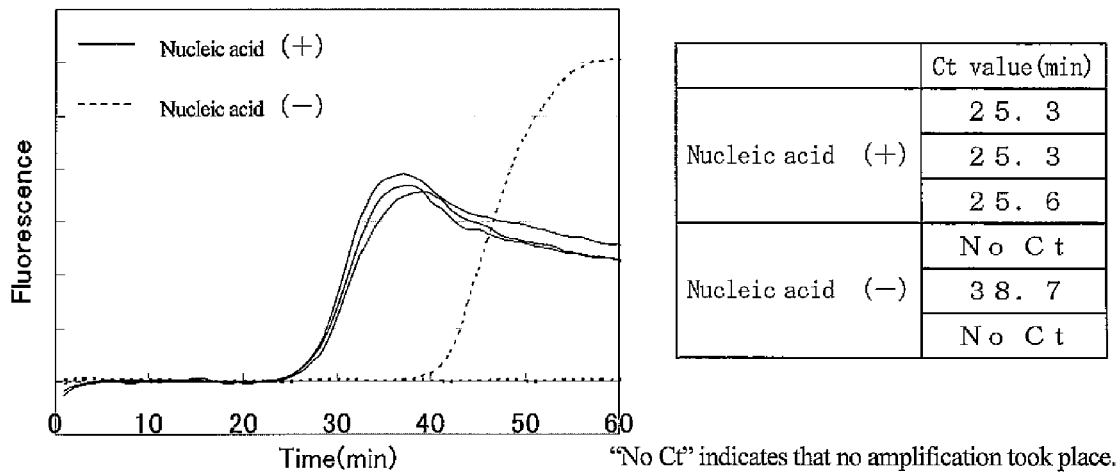
FIG. 7 shows the results of detecting amplified products of Level 1 (TWEEN® 20, 0.01%) in Example 2.
Figure 8:
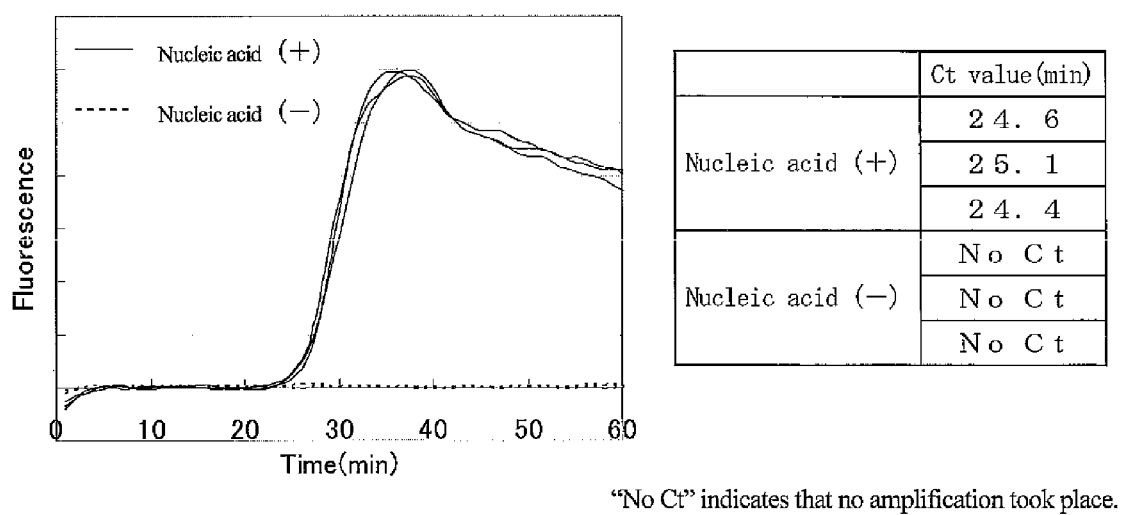
FIG. 8 shows the results of detecting amplified products of Level 2 (TWEEN® 20, 0.05%) in Example 2.
Figure 9:
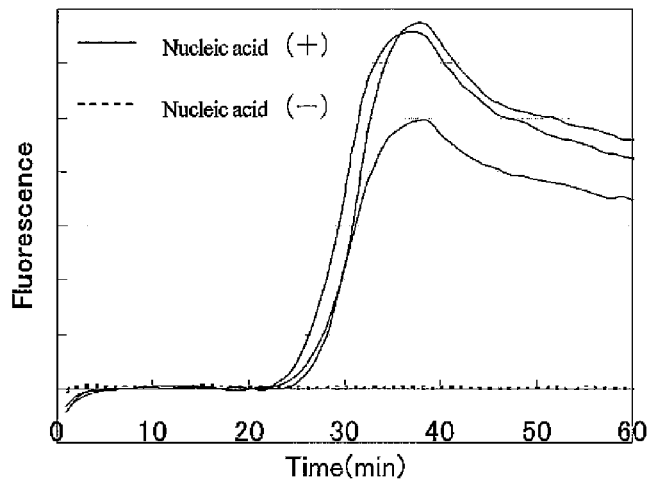
FIG. 9 shows the results of detecting amplified products of Level 3 (TWEEN® 20, 0.1%) in Example 2.
Figure 10:
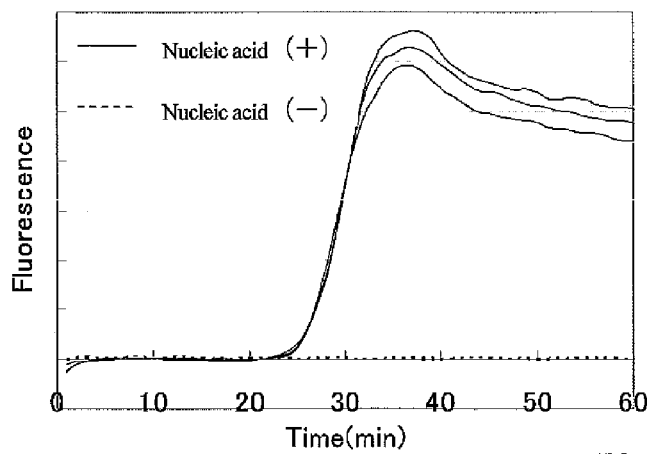
FIG. 10 shows the results of detecting amplified products of Level 4 (TWEEN® 20, 0.5%) in Example 2.
Figure 11:
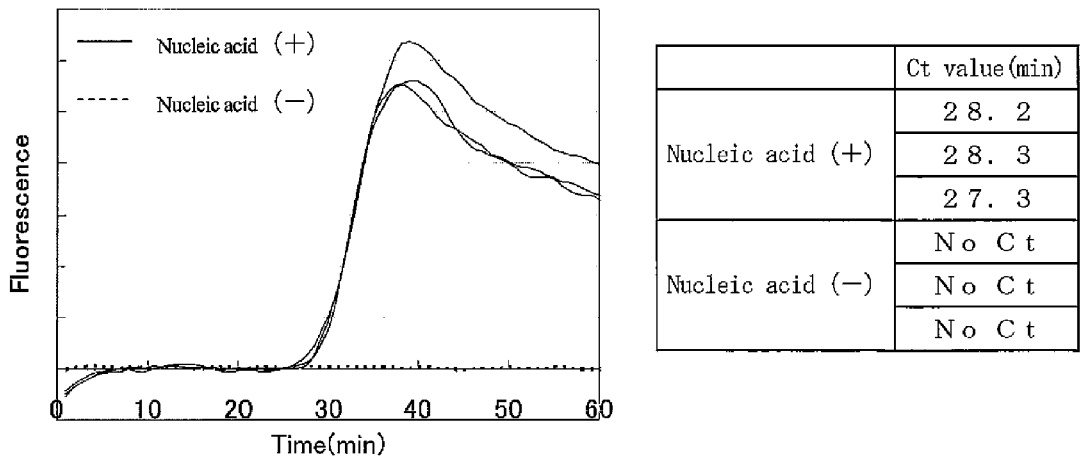
FIG. 11 shows the results of detecting amplified products of Level 1 (TWEEN® 40) in Example 3.
Figure 12:
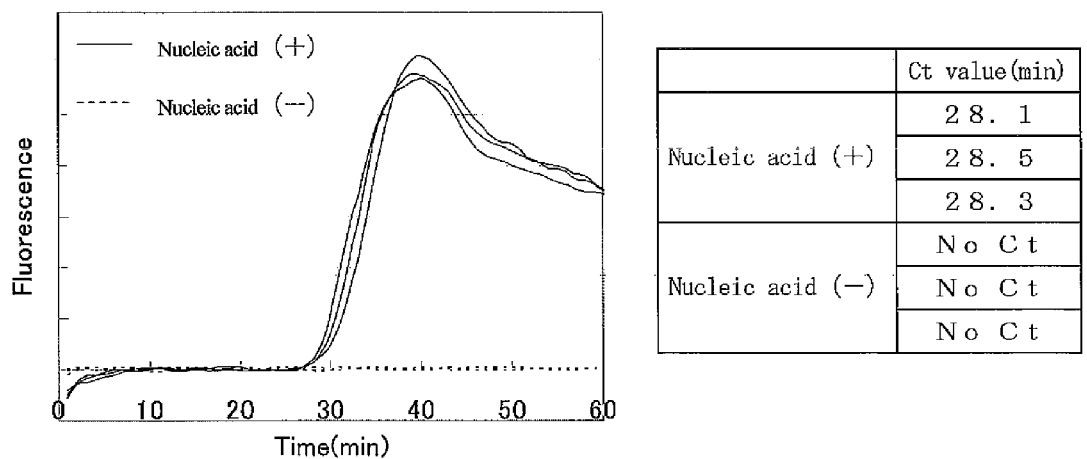
FIG. 12 shows the results of detecting amplified products of Level 2 (TWEEN® 60) in Example 3.
Figure 13:
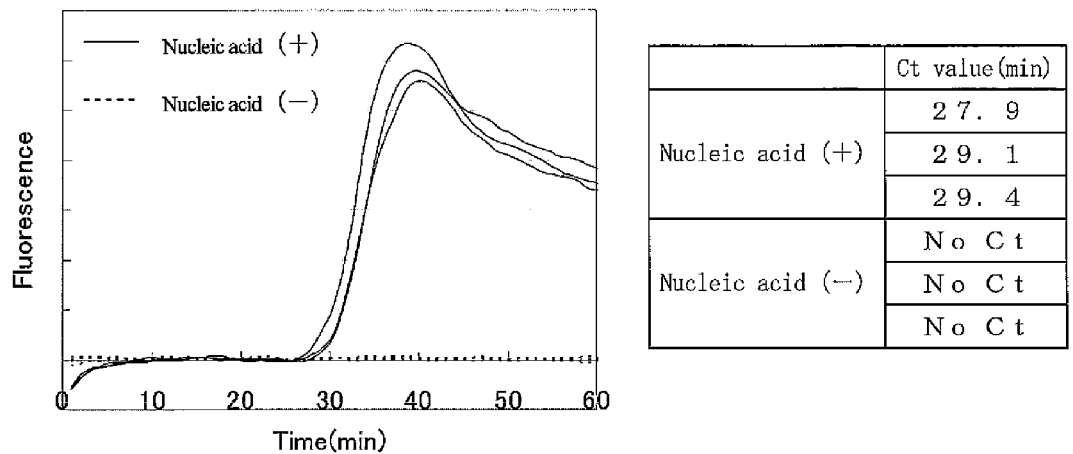
FIG. 13 shows the results of detecting amplified products of Level 3 (TWEEN® 80) in Example 3.
Figure 14:
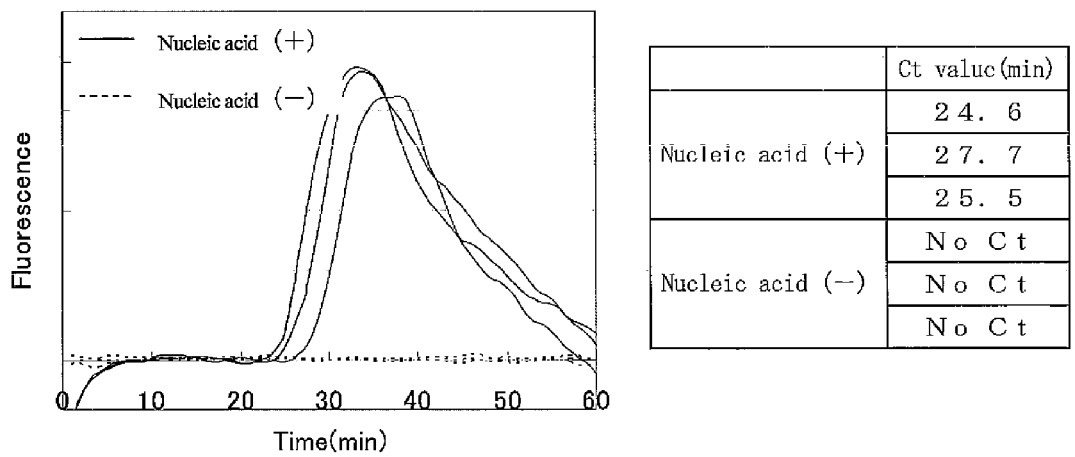
FIG. 14 shows the results of detecting amplified products of Level 4 (BRIJ® 35) in Example 3.
Figure 15:
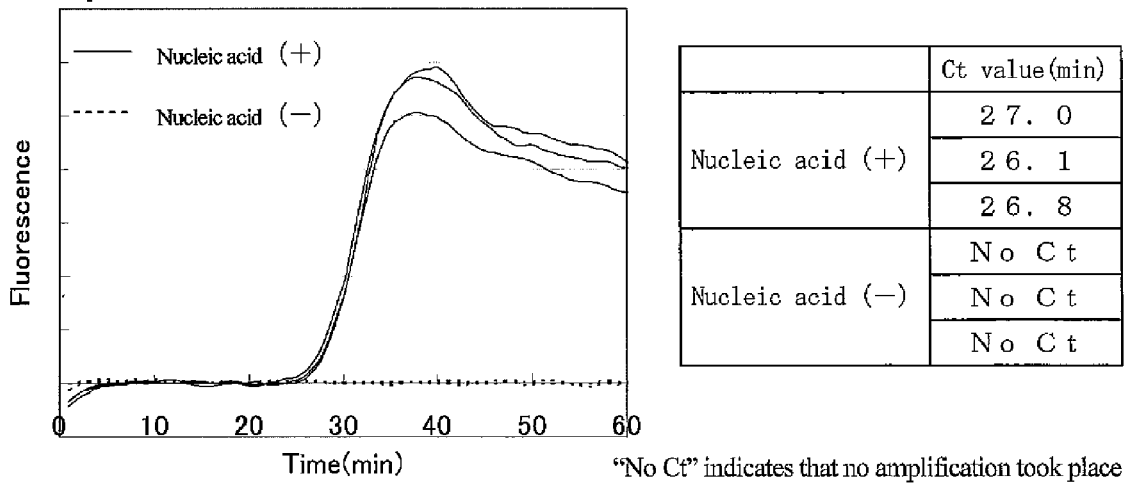
FIG. 15 shows the results of detecting amplified products of Level 5 (BRIJ® 56) in Example 3.
Figure 16:
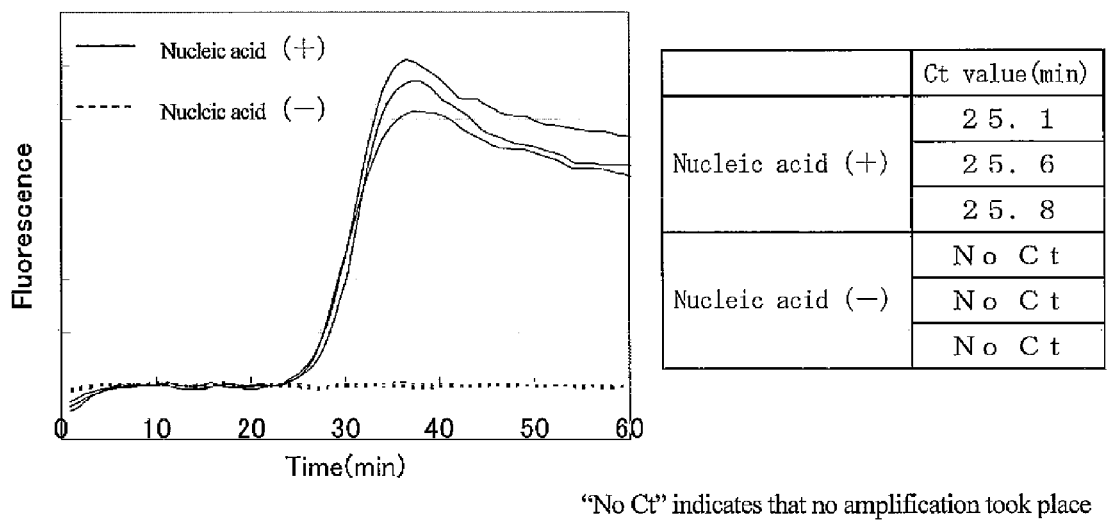
FIG. 16 shows the results of detecting amplified products of Level 6 (BRIJ® 700) in Example 3.
Figure 17:
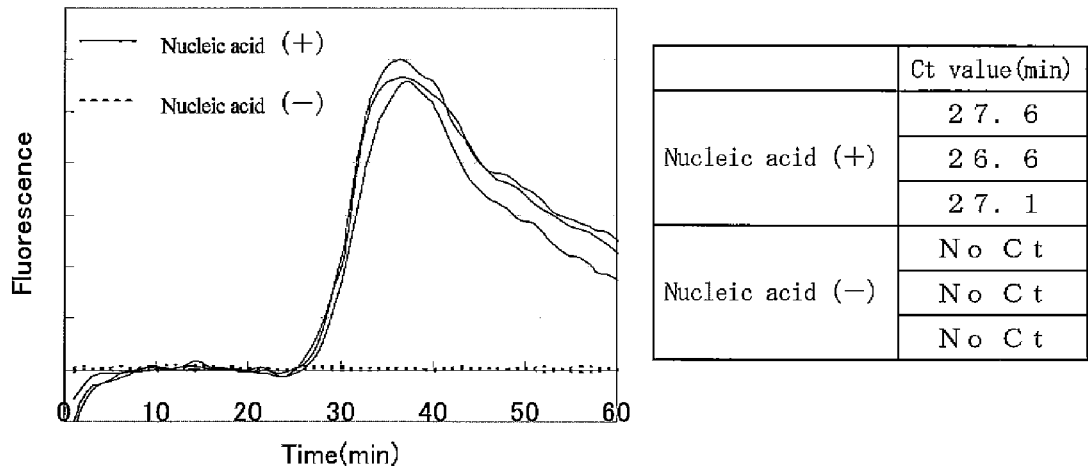
FIG. 17 shows the results of detecting amplified products of Level 7 (TRITON® X-100) in Example 3.
Figure 18:
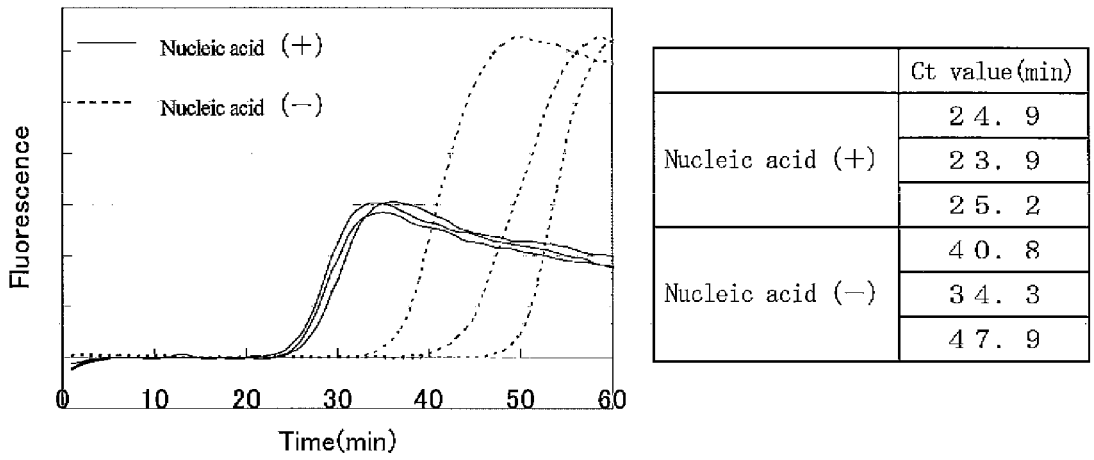
FIG. 18 shows the results of detecting amplified products of Level 8 (TWEEN® 85) in Example 3.
Figure 19:
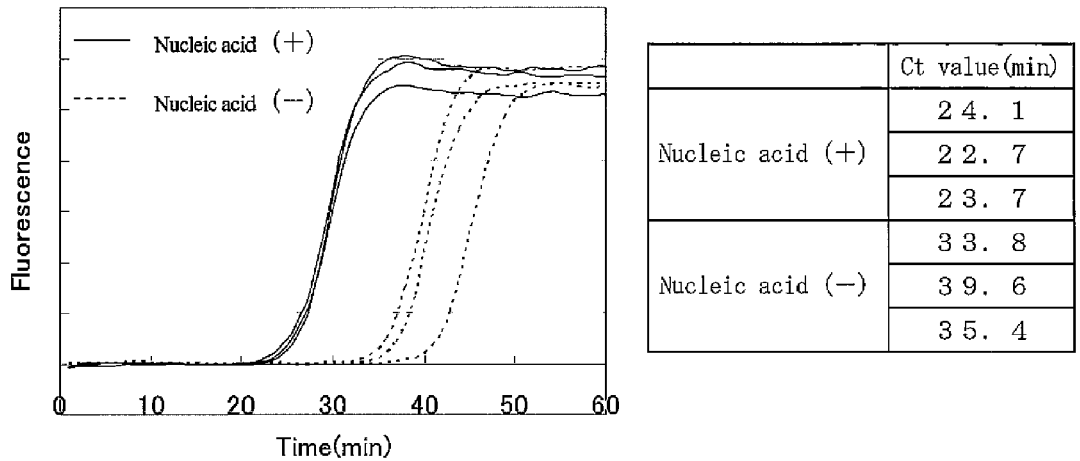
FIG. 19 shows the results of detecting amplified products of Level 9 (SPAN® 20 in Example 3.
Figure 20:
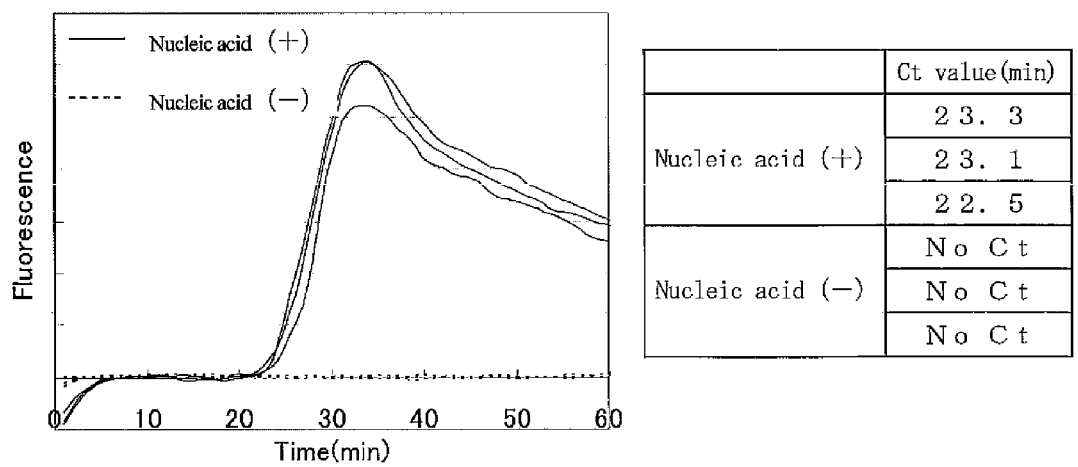
FIG. 20 shows the results of detecting amplified products of Level 1 (TWEEN® 40) in Example 4.
Figure 21:
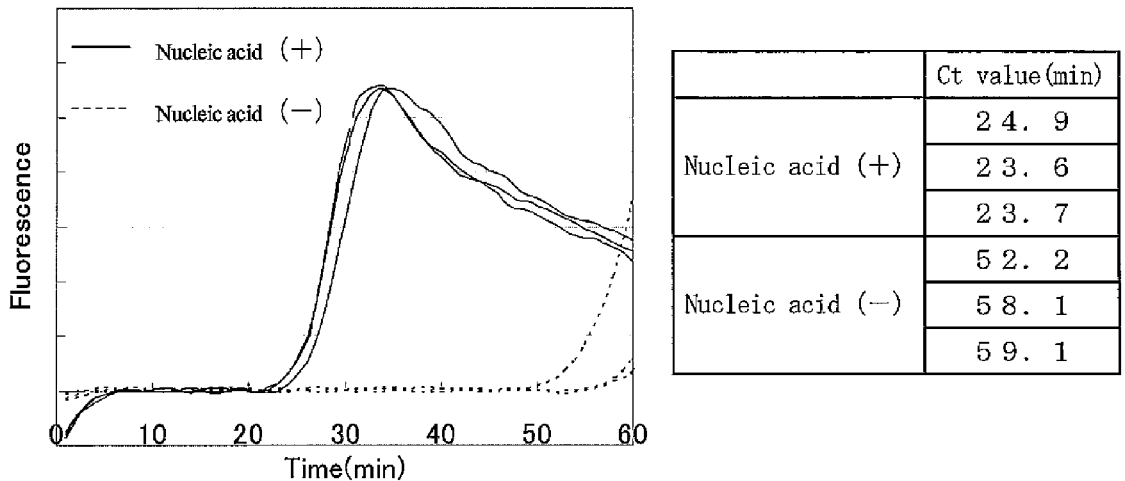
FIG. 21 shows the results of detecting amplified products of Level 2 (TWEEN® 60) in Example 4.
Figure 22:
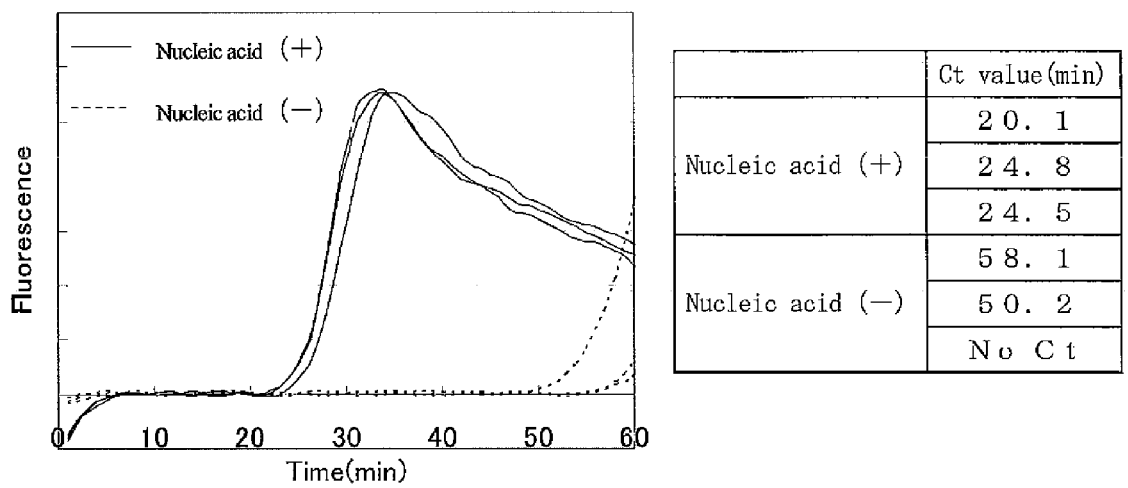
FIG. 22 shows the results of detecting amplified products of Level 3 (TWEEN® 80) in Example 4.
Figure 23:
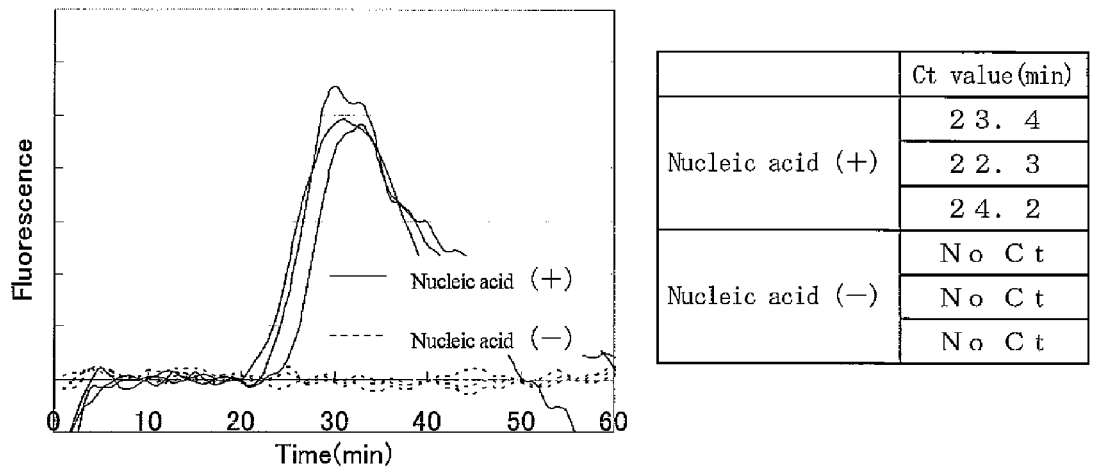
FIG. 23 shows the results of detecting amplified products of Level 4 (BRIJ® 35) in Example 4.
Figure 24:
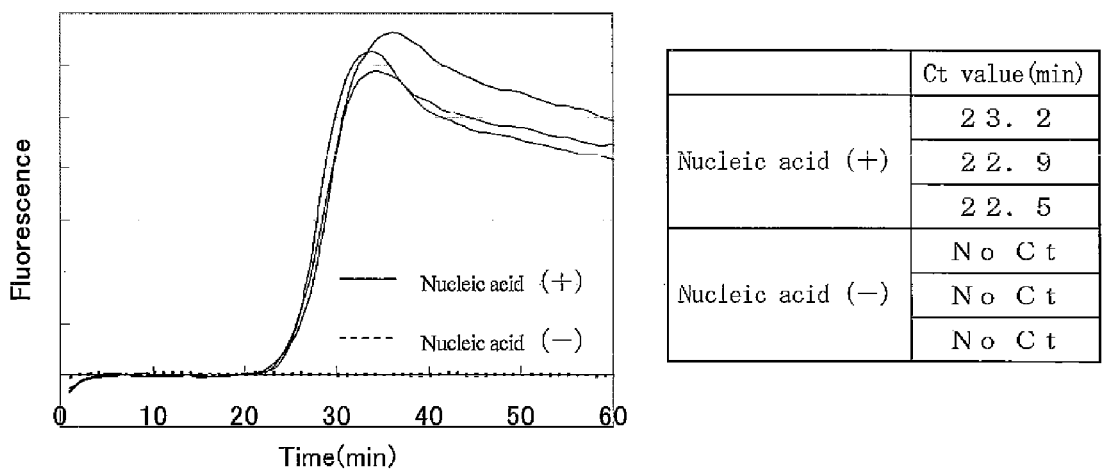
FIG. 24 shows the results of detecting amplified products of Level 5 (BRIJ® 56) in Example 4.
Figure 25:
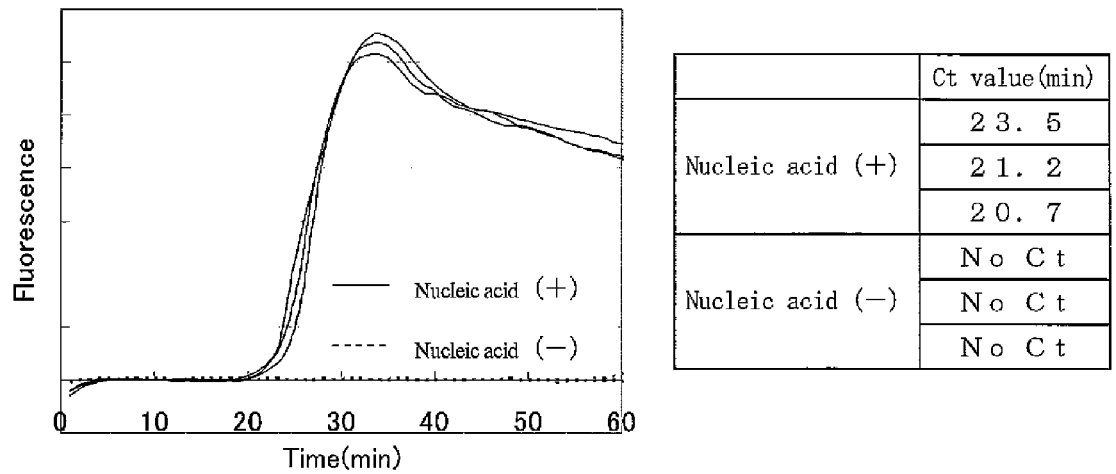
FIG. 25 shows the results of detecting amplified products of Level 6 (BRIJ® 700) in Example 4.
Figure 26:
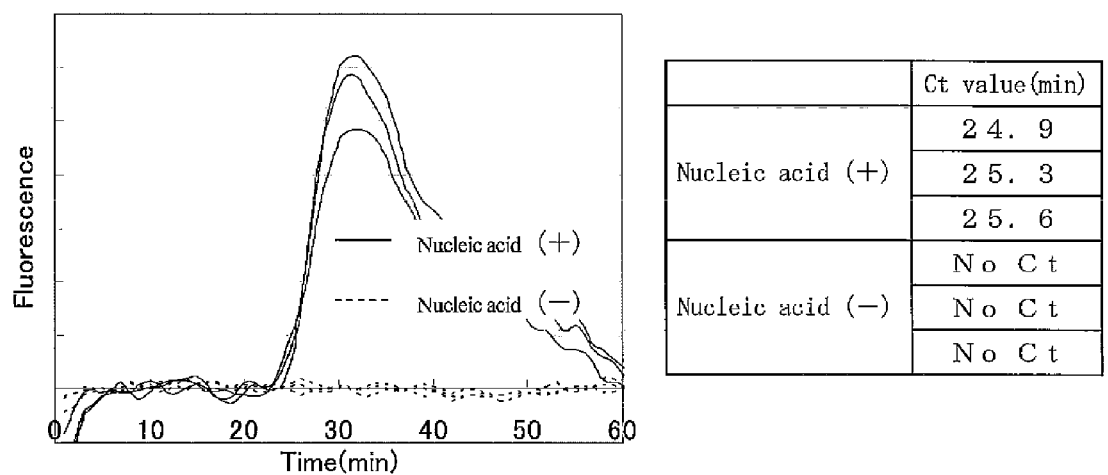
FIG. 26 shows the results of detecting amplified products of Level 7 (TRITON® X-100) in Example 4.
Figure 27:
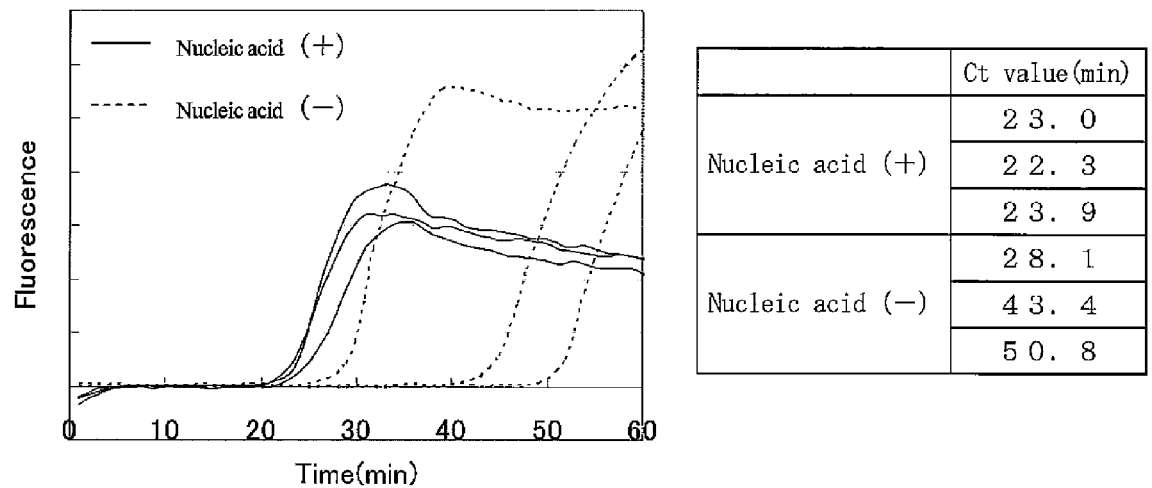
FIG. 27 shows the results of detecting amplified products of Level 8 (TWEEN® 85) in Example 4.
Figure 28:
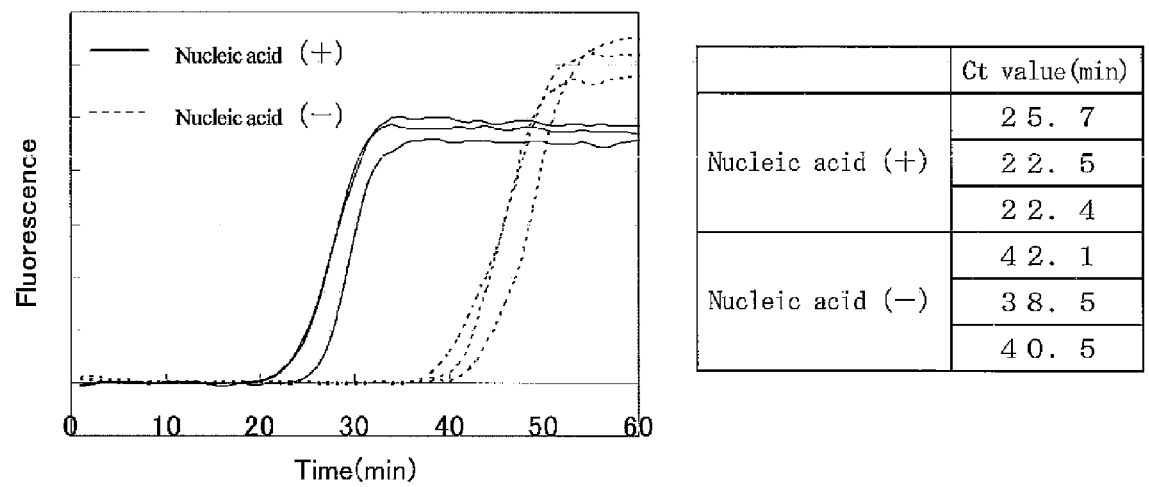
FIG. 28 shows the results of detecting amplified products of Level 9 (SPAN® 20) in Example 4.

The present invention will be further described in detail as follows.

According to the nucleic acid amplification method of the present invention, a reaction solution containing at least one type of deoxynucleotide triphosphate, at least one type of DNA polymerase having strand displacement activity, a divalent cation, at least one type of 0.01% or more surfactant, at least two types of oligonucleotide primer, and a nucleic acid fragment as a template is incubated substantially isothermally, so that a polymerase reaction that is initiated from the 3' end of the primer is carried out and thus the nucleic acid fragment is amplified.

According to a first aspect of the present invention, (a) one of at least two existing types of primer is annealed to a template nucleic acid strand and a synthesis reaction is initiated from the 3' end with the use of the strand displacement-type DNA polymerase so as to synthesize an elongation product; (b) oligonucleotide primers of a different type than the primers used in step (a) are caused to enter the double stranded nucleic acid obtained in the above step without performance of any denaturation of the double strands via application of a temperature higher than that in step (a), initiating a synthesis reaction from the 3' end by the action of the strand displacement-type DNA polymerase so as to synthesize an elongation product; (c) the same primers as those used in step (a) are annealed again to the nucleic acid liberated in step (b) above and a synthesis reaction is then initiated from the 3' end by the action of at least one type of strand displacement-type DNA polymerase, so as to synthesize an elongation product; and then (d) the double stranded nucleic acid obtained in step (b) above is used again in step (b).

According to a second aspect of the present invention, (a) one of at least two existing types of primer is annealed to a template nucleic acid strand and a synthesis reaction is initiated from the 3' end with the use of the strand displacement-type DNA polymerase so as to synthesize an elongation product; (b) oligonucleotide primers of the same type as the primers used in step (a) are caused to enter the double stranded nucleic acid obtained in the above step without performance of any denaturation of the double strands via application of a temperature higher than that in step (a), initiating a synthesis reaction from the 3' end by the action of the strand displacement-type DNA polymerase so as to synthesize an elongation product; (c) primers differing from those used in step (a) are annealed to the nucleic acid liberated in step (b) above and a synthesis reaction is then initiated from the 3' end by the action of at least one type of strand displacement-type DNA polymerase, so as to synthesize an elongation product; and then (d) the double stranded nucleic acid obtained in step (b) above is used again in step (b).

The amplification reaction of the present invention is characterized in that a reaction can be carried out by using a primer of simple structure as those used in the PCR method. In this amplification method, the annealing step of the primer to the template is performed isothermally as mentioned in the above (b). The equilibrium state of double strand and single strand is used, and it is important that a reaction is performed under an unstable condition of suitable double strand state. The reaction temperature is preferably 50° C. or more, and more preferably 55° C. or more. For example, incubation can be performed at 60° C. Preferred temperature range is for example about 50° C. to about 100° C., preferably about 50° C. to about 70° C., more preferably about 55° C. to about 65° C. Also, it is an important requirement that the primer is allowed to invade the unstable double strand efficiently. This efficacy can be achieved by controlling the length and concentration of the primer. The length of the oligonucleotide primer is not particularly limited, and is generally 10 to 100 nucleotides, preferably 15 to 50 nucleotides, more preferably 15 to 40 nucleotides. For example, an oligonucleotide of about 25 nucleotides can be used. The amount of the oligonucleotide in the reaction solution is preferably 0.1 µM to 100 µM, more preferably 1 µM to 50 µM, particularly preferably 1.5 µM to 10 µM. Generally, addition of the primer in a high concentration promotes the formation of non-specifically amplified product such as primer dimmer, but such formation can be effectively suppressed by addition of a surfactant in the present invention. The invading speed of the primer which is subjected to amplification can be increased by addition of a substance which assists the primer in invading. For example, another oligonucleotide may be designed at a near site, or DNA-binding protein such as single-strand binding protein or RecA may be used.

Further, the present invention is characterized in that not only a region between the primer pair such as in PCR is amplified as an amplification product although the primer such as those in the PCR method is used, and a long length product can be obtained as in the other isothermal amplification method. It is considered that this is because the synthesis of nucleic acid proceeds in the following mechanism.

Figure 35:
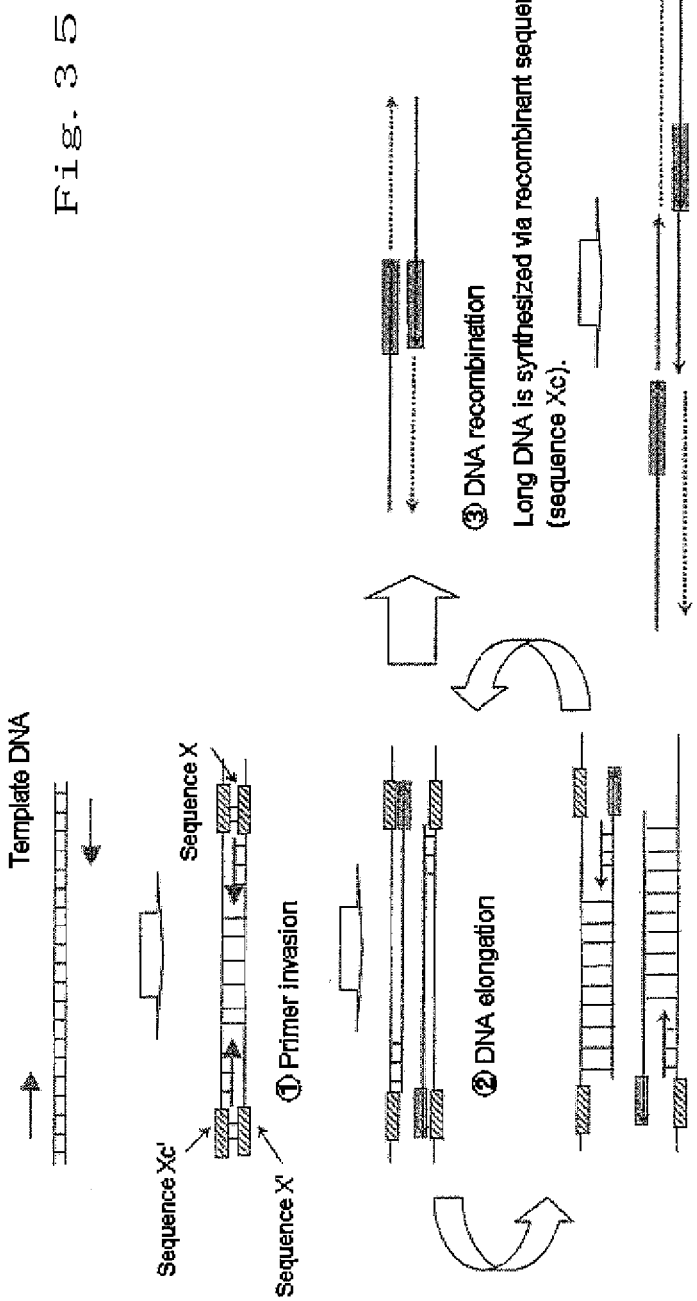
FIG. 35 shows the outline of the nucleic acid amplification method of the present invention.

The outline of the nucleic acid amplification method of the present invention is shown in FIG. 35. At least one of at least two existing types of primer is annealed to a template nucleic acid strand, and the polymerase reaction is initiated from the 3' end of the oligonucleotide primer. At this moment, if sequences X and X' of several nucleotides which are substantially identical are contained in a suitable position of 5' end and 3' end of the site to which the oligonucleotide of the nucleic acid sequence as a template is annealed, the amplification product which is initiated from this oligonucleotide primer contains a sequence X'c which is complementary to the sequence X'. at its 3' end (this is referred to as a nucleic acid fragment A). The sequences X and X' may be completely identical, or may be substantially identical so long as they can anneal with each other even if they are not completely identical. It is highly possible that sequences X and X' of several nucleotides which are substantially identical are contained in a suitable position of 5' end and 3' end of the site to which the oligonucleotide of the nucleic acid sequence as a template is annealed.

In the same way, the amplification product which is initiated from the other different oligonucleotide primer contains a sequence X at its 3' end (this is referred to as a nucleic acid fragment A). Then, the nucleic acid fragment A is hybridized to the nucleic acid fragment B via the sequences X and X'c, and elongation starts. Thus, a high molecular amplified nucleic acid fragment is synthesized. Further, the above-obtained nucleic acid fragment A is hybridized to the template nucleic acid fragment via the sequences X (sequence X'c), and elongation starts, and thus a high molecular amplified nucleic acid fragment is synthesized. Further, the above-obtained nucleic acid fragment B is hybridized to the template nucleic acid fragment via the sequences X' (sequence Xc), and elongation starts, and thus a high molecular amplified nucleic acid fragment is synthesized.

It is preferred that the sequences X and X' which are present at the 5' end and 3' end are identical as continuously as possible, but they may not completely identical and hybrid formation can be started. Namely, a region which is identical as highly as possible is selected from the sequences existing around the region to which the aforementioned primer is annealed. It is preferred that 4 or more nucleotides are identical, and it is more preferred that 7 or more nucleotides are identical. Although the upper limit of the number of the identical nucleotides is not particularly limited, it is generally 15 or less nucleotides, more generally 10 or less nucleotides. The match ratio of the sequences X and Xc' is preferably 50% or more, and more preferably 70% or more, and still preferably 90% or more.

Hereinafter, ingredients that are used in the present invention will be explained.

(1) Deoxynucleotide Triphosphate

Deoxynucleotide triphosphate is used as a substrate for an elongation reaction. Specifically, a mixture of dATP, dCTP, dGTP, and dTTP is preferably used. Deoxynucleotide triphosphate to be used herein may contain a dNTP analog (e.g., 7-deaza-dGTP).

Furthermore, deoxynucleotide triphosphate (dATP, dCTP, dGTP, or dTTP mixture) is at a final concentration ranging from 0.1 mM to 3.0 mM, preferably 0.75 mM to 3.0 mM, further preferably 1.0 mM to 2.0 mM, and particularly preferably 1.0 mM to 1.5 mM.

(2) Polymerase Capable of Strand Displacement

In the present invention, polymerase capable of strand displacement (or having strand displacement activity) is used. In the description, "strand displacement activity" refers to activity by which strand displacement can be performed; that is, when DNA replication is performed based on a template nucleic acid sequence, strand displacement proceeds by replacement of DNA strands, so as to liberate a complementary strand that has annealed to the template strand. Specific examples of polymerase capable of strand displacement include, but are not limited to, *Bacillus stearothermophilus*-derived 5'→3' exonuclease-deficient Bst. DNA polymerase, *Bacillus caldotenax*-derived 5'→3' exonuclease-deficient Bca DNA polymerase, and *Thermococcus litoralis*-derived 5'→3' exonuclease-deficient Vent. DNA polymerase. Such polymerase capable of strand displacement may be derived from nature or may be a genetically engineered recombinant protein.

(3) Divalent Cation

In the present invention, divalent cations are used in response to metal requirements and the like regarding enzymes to be used herein. As divalent cations, magnesium salts or other metal salts can be used. For example, magnesium chloride, magnesium acetate, and magnesium sulfate can be used. Such a divalent cation is at a final concentration preferably ranging from 1 mM to 20 mM and further preferably ranging from 2 mM to 10 mM.

(4) Surfactant

In the present invention, a surfactant is added to a reaction solution. An advantageous effect of the present invention; that is, prevention of nonspecific nucleic acid amplification, is achieved via the use of a surfactant. Types of such surfactant that can be used in the present invention are not particularly limited, and may include the following:

anionic surfactants such as alkylbenzene sulfonate, lauryl sulfate (SDS), octyl sulfosuccinate, and stearic acid soap;
nonionic surfactants such as sorbitan fatty acid ester, POE sorbitan fatty acid ester (e.g., TWEEN®), POE alkyl ether (e.g., BRIJ®), POE alkyl phenyl ether (e.g., TRITON®), nonylphenol, lauryl alcohol, polyethylene glycol, polyoxyethylene.polyoxypropylene block polymer, POE alkyl amine, and POE fatty acid bisphenyl ether;
cationic surfactants such as cetylpyridium chloride, lauryl dimethylbenzyl ammonium chloride, and stearyltrimethylammonium chloride; and ampholytic surfactants such as alkyldimethylamine oxide and alkylcarboxybetaine.

The dose of such a surfactant is not particularly limited, as long as the effects of the present invention can be achieved and is preferably 0.01% or more, more preferably 0.05% or more, and more preferably 0.1% or more. The upper limit of the dose of such a surfactant is not particularly limited and is generally 10% or less, preferably 5% or less, and more preferably 1% or less.

Among the above surfactants, nonionic surfactants are preferably used. Among the nonionic surfactants, highly hydrophilic surfactants are preferred. The HLB value is preferably 12 or more, and further preferably 14 or more. Preferably, the upper limit of HLB is 20. Preferably, the value of HLB is 17 or less. More preferably, the value of HLB is 14 to 17. The surfactant is preferably selected from a polyoxyethylene sorbitan fatty acid ester-based surfactant, and a polyoxyethylene alkyl ether-based surfactant. Among the polyoxyethylene sorbitan fatty acid ester, polyoxyethylene sorbitan mono fatty acid ester is preferred. Preferably the compound represented by the following formula can be used:

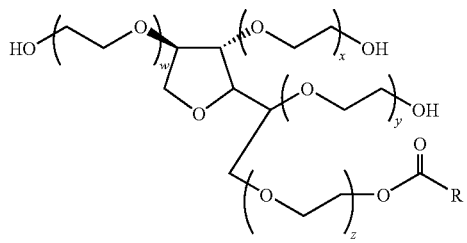

wherein $x+y+z+w=20$, R is an alkyl group having a carbon number of 12 to 18.

The position of the alkyl group is not particularly limited, and the compound of the following structure can be preferably used.

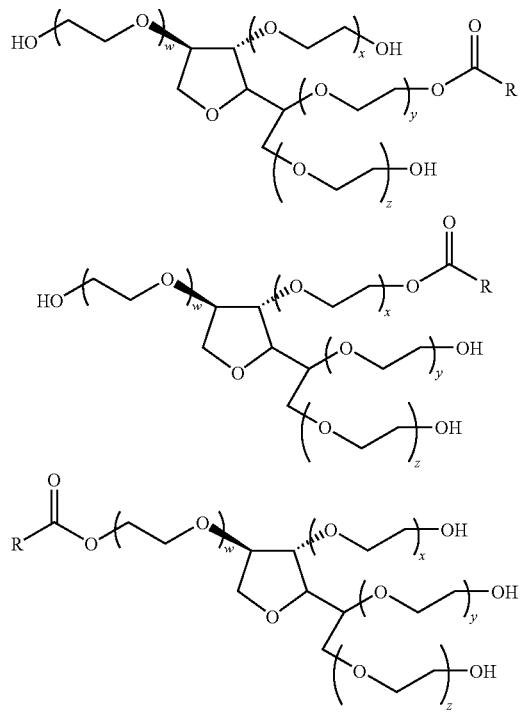

wherein $x+y+z+w=20$, R is an alkyl group having a carbon number of 12 to 18.

Specific examples of such surfactants may include polyoxyethylene(20) sorbitan monolaurate, polyoxyethylene(20) sorbitan monopalmitate, polyoxyethylene(20) sorbitan monostearate, and polyoxyethylene(20) sorbitan monooleate (trade name: TWEEN® 20, TWEEN® 40, TWEEN® 60, TWEEN® 80, and the like). The dose of such surfactant is not particularly limited, and may be preferably 0.01% or more, more preferably 0.05% or more, and more preferably 0.1% or more.

(5) Oligonucleotide Primer (a) A Set of at Least Two Types of Oligonucleotide Primer At least two types of oligonucleotide primer to be used in the present invention has a nucleotide sequence substantially complementary to template DNA and has the 3' end from which DNA strand elongation is possible. Such oligonucleotide primer has a nucleotide sequence substantially complementary to template DNA, so that it can anneal to the template DNA. As an oligonucleotide primer to be used in the present invention, an oligonucleotide primer composed of a deoxyribonucleotide or a ribonucleotide can be used. Furthermore, an oligonucleotide primer containing a modified ribonucleotide or a modified deoxyribonucleotide may also be used herein.

For the aforementioned oligonucleotide primer, no complicated design such as those employed for conventional isothermal amplification reactions is required. An important feature of the present invention is resides in that isothermal amplification reactions can be carried out by using at least one set of primers which are used in the general PCR. Especially, these primers do not have a structure which forms a loop structure wherein 5' terminal is complementary to the region which was elongated from the 3' terminal as used in LAMP method. Namely, the consecutive region at 3'-terminal of the primer is complementary to the template nucleic acid. Further, the oligonucleotide primer has no complicated system where the primer is cleaved during the reaction and the cleaved 3' terminal serves as a synthesis origin, which is used in the SDA method or the ICAN method.

The length of an oligonucleotide primer is not particularly limited and generally ranges from approximately 10 to 100 nucleotides, preferably ranges from approximately 15 to 50 nucleotides, and further preferably ranges from approximately 15 to 40 nucleotides.

Oligonucleotide primers can be synthesized by the phosphoamidite method using a commercially available DNA synthesizer (e.g., Applied Biosystem Inc., DNA synthesizer 394).

The dose of an oligonucleotide primer is preferably 0.1 μM to 100 μM, further preferably 1 μM to 50 μM, and particularly preferably 1.5 μM to 10 μM in a reaction solution.

It is preferred that at least one primer of the aforementioned set of at least two types of oligonucleotide primer is a forward primer, and at least one primer of the aforementioned set of at least two types of oligonucleotide primer is a reverse primer.

(b) Additional Oligonucleotide Primer

In the present invention, not only the aforementioned at least two types of oligonucleotide primers, but also one or more types of additional oligonucleotide primers may be further added to the reaction solution, so as to perform the reaction. By using such additional oligonucleotide primer, amplification speed can be increased as the primer is added. Therefore, 3 types or more primers are preferably used. The additional primer may be a forward primer or a reverse primer.

Preferably, such one or more types of additional oligonucleotide primers can be selected such that regions on the template, to which the aforementioned at least two types of oligonucleotide primers and the one or more types of additional oligonucleotide primers are annealed, can be positioned in regions within 1000 bp on the template.

The length of an additional oligonucleotide primer used in the present invention is not particularly limited and generally ranges from approximately 10 to 100 nucleotides, preferably ranges from approximately 15 to 50 nucleotides, and further preferably ranges from approximately 15 to 40 nucleotides.

The additional oligonucleotide primers used in the present invention can be synthesized by the phosphoamidite method using a commercially available DNA synthesizer (e.g., Applied Biosystem Inc., DNA synthesizer 394).

The dose of an additional oligonucleotide primer used in the present invention is preferably 0.1 μM to 100 μM, further preferably 1 μM to 50 μM, and particularly preferably 1.5 μM to 10 μM.

(6) Template Nucleic Acid Fragment

In the present invention, template nucleic acid (DNA or RNA) may be any of genomic DNA, cDNA, synthetic DNA, mRNA, and total RNA. Nucleic acid that is prepared from a sample that may contain template nucleic acid may also be used. A sample that may contain template nucleic acid may also be directly used intact. Examples of the type of a sample containing template nucleic acid are not particularly limited and include body fluids (e.g., whole blood, serum, urine, cerebrospinal fluid, seminal fluid, and saliva), tissues (e.g., cancer tissue), in vivo derived samples such as cell culture products, nucleic acid-containing samples such as viruses, bacteria, fungi, yeast, plants, and animals, samples that may be contaminated with microorganisms (e.g., foods), or samples in an environment such as soil or waste water. When nucleic acid is prepared from a sample described above, the preparation method therefor is not particularly limited. For example, methods known by persons skilled in the art can be used, including treatment using a surfactant, ultrasonication, purification using glass beads, and the like. Purification of nucleic acid from such a sample can be performed by phenol extraction, chromatography, gel electrophoresis, density gradient centrifugation, or the like.

For amplification of nucleic acid having an RNA-derived sequence, the method of the present invention can be implemented using cDNA as a template that is synthesized by a reverse transcription reaction using the RNA as a template. A primer to be used for a reverse transcription reaction may be a primer having a nucleotide sequence complementary to a specific template RNA, an oligo dT primer, or a primer having a random sequence. The length of a primer for reverse transcription preferably ranges from approximately 6 to 100 nucleotides and further preferably ranges from 9 to 50 nucleotides. Examples of an enzyme that can be used for a reverse transcription reaction are not particularly limited, as long as such an enzyme has activity of synthesizing cDNA with the use of template RNA and include avian myeloblastosis virus-derived reverse transcriptase (AMV RTase), moloney murine leukemia virus-derived reverse transcriptase (MMLV RTase), and rous associated virus 2 reverse transcriptase (RAV-2 RTase). Furthermore, strand displacement-type DNA polymerase that also has reverse transcription activity can also be used.

In the present invention, double-stranded DNA such as genomic DNA or a nucleic acid amplification fragment and single-stranded DNA such as cDNA that is prepared from RNA via a reverse transcription reaction can be used as template DNAs. The above double-stranded DNA can be used for the method of the present invention after it has been denatured to single-stranded DNAs or can also be used for the method of the present invention without performing such denaturation.

(7) Melting Temperature Adjusting Agent

A melting temperature adjusting agent can be added to a reaction solution to be used in the present invention. Specific examples of such a melting temperature adjusting agent include dimethyl sulfoxide (DMSO), betaine, formamide or glycerol, tetraalkyl ammonium salt, and a mixture of two or more types thereof. The dose for melting temperature adjustment is not particularly limited. In the case of DMSO, formamide, or glycerol, a melting temperature adjusting agent can be generally contained accounting for 10% or less of a reaction solution.

Betaine or tetraalkyl ammonium salt can be added at a concentration ranging from approximately 0.2 M to 3.0 M, preferably approximately 0.5 M to 1.5 M.

(8) Buffer Component

A reaction solution in the present invention can contain a buffer component. Examples of such a buffer component that can be used herein include, but are not particularly limited to, bicin, tricine, hepes, tris, and phosphate (e.g., sodium phosphate and potassium phosphate). The final concentration of such a buffer component ranges from 5 mM to 100 mM and particularly preferably ranges from 10 mM to 50 mM. Regarding pH, such a buffer component having pH generally ranging from 6.0 to 9.0 and particularly preferably ranging from 7.0 to 9.0 can be used, depending on optimum pH for an enzyme to be used for an amplification reaction.

(9) Nucleic Acid Amplification Method According to the Present Invention

Next, the nucleic acid amplification method according to the present invention will be described. According to the present invention, a reaction solution containing at least one type of deoxynucleotide triphosphate, at least one type of DNA polymerase having strand displacement activity, a divalent cation, at least one type of nonionic surfactant, at least two types of oligonucleotide primer, and a template nucleic acid fragment is incubated substantially isothermally. Thus, a polymerase reaction that initiates from the 3' end of the primer is performed, so that the nucleic acid fragment can be amplified. A temperature for incubation of the reaction solution is preferably 50° C. or higher and more preferably 55° C. or higher. For example, incubation can be performed at approximately 60° C. Preferably the temperature ranges from approximately 50° C. to approximately 70° C. and further preferably ranges from approximately 55° C. to approximately 65° C., for example. In this case, nonspecific annealing of the primers is suppressed, specificity for DNA amplification is improved, and the secondary structure of template DNA is dissolved. Hence, the elongation activity of DNA polymerase is also improved. The nucleic acid amplification method according to the present invention can be implemented substantially isothermally. "Isothermal or isothermally" in the present invention means that each step is performed at a substantially constant temperature without any significant changes in reaction temperature of each step.

In the present invention, the time required for substantially isothermal incubation of a reaction solution is not particularly limited, as long as a target nucleic acid fragment can be amplified. The time for incubation can be determined to be 5 minutes or more and 12 hours or less, for example. The time for incubation is preferably 5 minutes or more and 2 hours or less, more preferably 5 minutes or more and 60 minutes or less, and further preferably 5 minutes or more and 30 minutes or less. The time for incubation can also be 5 minutes or more and 15 minutes or less.

The nucleic acid amplification method according to the present invention is characterized in that there is no need to raise or lower the temperature for a nucleic acid synthesis method. Conventional PCR methods require to raise or lower the temperature. For example, such conventional PCR methods require a reaction apparatus such as a thermal cycler. However, the method of the present invention can be implemented with only an apparatus capable of maintaining a constant temperature.

(10) Application of the Nucleic Acid Amplification Method According to the Present Invention The nucleic acid amplification method according to the present invention can be used for nucleic acid detection, labeling, nucleotide sequence determination, detection of nucleotide mutation (including detection of single nucleotide polymorphism, for example), and the like. The nucleic acid amplification method of the present invention does not require the use of a reaction apparatus capable of performing temperature regulation. Thus, an amplification reaction can be performed according to the method using a large amount of a reaction solution.

Amplified products obtained by the use of the nucleic acid amplification method of the present invention can be detected by methods known by persons skilled in the art. For example, according to gel electrophoresis, gel is stained with ethidium bromide and then reaction products of a specific size can be detected. As detection systems for detection of amplified products, fluorescence polarization, immunoassay, fluorescent energy transfer, enzyme labels (e.g., peroxidase and alkaline phosphatase), fluorescent labels (e.g., fluorescein and rhodamine), chemiluminescence, bioluminescence, or the like can be used. Amplified products can also be detected using a labeled nucleotide labeled with biotin or the like. In such a case, biotin in an amplified product can be detected using fluorescence labeled avidin, enzyme-labeled avidin, or the like.

The present invention will be specifically described in the following examples. However, the examples are not intended to limit the present invention.

EXAMPLES

Example 1

Amplification of Target Nucleic Acid Sequence in Human Gene (1) Preparation of Nucleic Acid Specimen Solution Containing Target Nucleic Acid Fragment 7.5 ng of Human Genomic DNA (produced by Clontech) was heated at 98° C. for 3 minutes, and then a specific sequence in the target nucleic acid was amplified under the following conditions. As a negative control, a sample was also prepared by heating water under the same conditions.

<Primers>

The following 4 types of primers were designed, and purchased from Operon Biotechnologies. Each primer sequence is as shown below. Primers (1) and (2) are sequences of β-actin, and Primers (3) and (4) are complementary to sequences of β 2AR gene.

```
Primer (1):
5'-GGGCATGGGTCAGAAGGATT-3'       (SEQ ID NO: 1)

Primer (2):
5'-CCTCGTCGCCCACATAG-3'          (SEQ ID NO: 2)

Primer (3):
5'-CTTGCTGGCACCCAATA-3'          (SEQ ID NO: 3)

Primer (4):
5'-CCGGCGCATGGCTT-3'             (SEQ ID NO: 4)
```

<Surfactant>

TWEEN® 20 (Wako Pure Chemical Industries, Ltd.) was used as a surfactant. TWEEN® 20 is polyoxyethylene(20) sorbitan monolaurate, and is a polyoxyethylene sorbitan fatty acid ester-based non-ionic surfactant. TWEEN® 20 has HLB of 16.7, and is represented by the following formula.

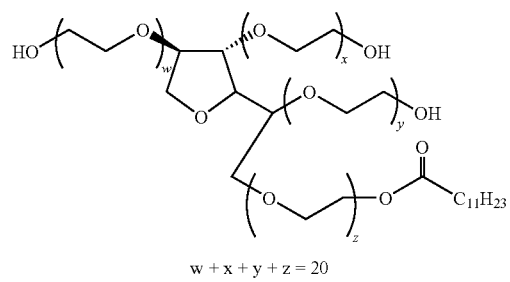

$w + x + y + z = 20$ (2) Nucleic Acid Amplification Reaction

The amplification reaction was performed with the composition of a reaction solution shown below at 60° C. for 60 minutes. Bst. DNA polymerase (NEB (New England Biolabs)) was used as an enzyme.

<Composition of Reaction Solution>

| | |
|---|---|
| 10 × Bst Buffer (DF) | 2.5 μL |
| 100 mM MgSO4 | 1.5 μL |
| 10% (v/v) TWEEN ® 20 or purified water | 0.25 μL |
| 100% DMSO | 1.25 μL |
| 25 mM dNTP each | 1.4 μL |
| SYBR ® Green · (2000 times) | 0.5 μL |
| 50 μM forward primer | 1.6 μL |
| 50 μM reverse primer | 1.6 μL |
| Bst. Polymerase | 1.0 μL |
| Nucleic acid fragment specimen solution obtained in (1), or purified water | 1.0 μL |
| Purified water | 12.4 μL |
| | 25.0 μL |

In Levels 1 and 2, the following combination of forward primer and reverse primer was used.

Level 1 and Level 2 forward primer: primer (1)

reverse primer: primer (2)

In Levels 3 and 4, the following combination of forward primer and reverse primer was used.

Level 3 and Level 4 forward primer: primer (3)

reverse primer: primer (4)

In Level 1 and Level 3, TWEEN® 20 was added as a surfactant.

In Level 2 and Level 4, purified water was added in place of a surfactant.

In each Level, 4 samples containing nucleic acid specimen, and 4 samples containing purified water in place of nucleic acid specimen (negative control) were prepared.

(3) Detection of Amplified Product

The amplification reaction in (2) above was carried out using a real-time fluorescence detection apparatus (MX3000P®, produced by Stratagene), and the fluorescent intensity was measured with time to detect the amplification. FIGS. 1 to 4 show the results. On the right of the figures, the time (Ct value, minutes) when an amount of fluorescence had reached 250 in the above graph was shown.

In Level 1 and Level 3 where a surfactant was added, amplification was detected only in the samples containing nucleic acid specimen. Namely, nucleic acid specimen can be detected using this amplification method.

In Level 2 and Level 4 where a surfactant was not added, amplification was detected also in the samples containing no nucleic acid specimen (negative control). Namely, nucleic acid specimen can not be detected using this amplification method.

Since the same result was obtained using different primers, it was confirmed that the effect of a surfactant does not depend on the primer, but is a universal effect.

FIG. 5 shows the result of electrophoresis of amplified product in Level 1. Electrophoresis was carried out using 2% agarose gel and TAE buffer Electrophoresis period was 40 minutes.

It was confirmed that amplified product was obtained only in samples containing nucleic acid specimen. Also, it was confirmed that amplified product of high molecular weight having various strand lengths was obtained. Almost similar electrophoresis patterns were obtained in 4 samples.

FIG. 6 shows the result of electrophoresis of amplified product in Level 2. Electrophoresis was carried out using 2% agarose gel and TAE buffer. Electrophoresis period was 40 minutes.

It was confirmed that amplified product was obtained also in samples containing no nucleic acid specimen (negative control). Also, amplified product did not show certain electrophoresis pattern.

The amplified product having the shortest strand length in Level 1 was cut out of the gel, and was cloned using TOPO cloning kit (Invitogen). Then, sequencing was carried out to determine the sequence of the amplified product.

It was confirmed that amplified product having the sequence of SEQ ID NO:5 was obtained in Level 1.

```
                                              (SEQ ID NO: 5)
5'-GGGCATGGGTCAGAAGGATTCCTATGTGGGCGACGAGG-3'
```

This is a sequence composed of a region complementary to Primer (1) used in Level 1, a region complementary to Primer (2), and a region between these primers.

From the above, it was confirmed that amplified product was obtained as a result that the primers recognized the target nucleic acid in a sequence-specific manner.

Example 2

Effect of Concentration of the Surfactant (1) Preparation of Nucleic Acid Specimen Solution Containing Target Nucleic Acid Fragment 7.5 ng of HumanGenomic DNA (produced by Clontech) was heated at 98° C. for 3 minutes, and then a specific sequence in the target nucleic acid was amplified under the following conditions. As a negative control, a sample was also prepared by heating water under the same conditions.

<Primers>

Primers (1) and (2) used in Example 1 were used as the primer.

```
Primer (1):
5'-GGGCATGGGTCAGAAGGATT-3'       (SEQ ID NO: 1)

Primer (2):
5'-CCTCGTCGCCCACATAG-3'          (SEQ ID NO: 2)
```

<Surfactant>

TWEEN® 20 (Wako Pure Chemical Industries, Ltd.) was used as a surfactant.

(2) Nucleic Acid Amplification Reaction

The amplification reaction was performed with the composition of a reaction solution shown below at 60° C. for 60 minutes. Bst. DNA polymerase (NEB (New England Biolabs)) was used as an enzyme.

<Composition of Reaction Solution>

| | |
|---|---|
| 10 × Bst Buffer (Detergent Free) | 2.5 μL |
| 100 mM MgSO4 | 1.5 μL |
| 10% (v/v) surfactant | 0.25 μL |
| 100% DMSO | 1.25 μL |
| 25 mM dNTP each | 1.4 μL |
| SYBR ® Green · (2000 times) | 0.5 μL |
| 50 μM primer (1) | 1.6 μL |
| 50 μM primer (2) | 1.6 μL |
| Bst. Polymerase | 1.0 μL |
| Nucleic acid fragment specimen obtained in (1), or purified water | 1.0 μL |
| Purified water | 12.4 μL |
| | 25.0 μL |

Experiments were carried out in total 4 Levels where the final concentration of TWEEN® 20 was adjusted as follows.
Level 1: The final concentration of TWEEN® 20 is 0.01%.
Level 2: The final concentration of TWEEN® 20 is 0.05%.
Level 3: The final concentration of TWEEN® 20 is 0.1%.
Level 4: The final concentration of TWEEN® 20 is 0.5%.

In each Level, 3 samples containing nucleic acid specimen, and 3 samples containing purified water in place of nucleic acid specimen (negative control) were prepared.

(3) Detection of Amplified Product

The amplification reaction in (2) above was carried out using a real-time fluorescence detection apparatus (MX3000P®, produced by Stratagene), and the fluorescent intensity was measured with time to detect the amplification. FIGS. 7 to 10 show the results. On the right of the figures, the time (Ct value, minutes) when an amount of fluorescence had reached 250 in the above graph was shown.

In the case where the final concentration of TWEEN® 20 is 0.01% (Level 1), amplification was detected in 1 sample among 3 samples of negative control. However, since Ct value is largely different from the case of sample containing nucleic acid, the presence of nucleic acid specimen can be detected by this amplification method.

In the cases where the final concentration of TWEEN® 20 is 0.05% or more (Levels 2 to 4), amplification was detected only in samples containing nucleic acid. Namely, the presence of nucleic acid specimen can be detected by this amplification method.

Example 3

Effect of Type of the Surfactant (1) Preparation of Nucleic Acid Specimen Solution Containing Target Nucleic Acid Fragment 7.5 ng of HumanGenomic DNA (produced by Clontech) was heated at 98° C. for 3 minutes, and then a specific sequence in the target nucleic acid was amplified under the following conditions. As a negative control, a sample was also prepared by heating water under the same conditions.

<Primers>

Primers (1) and (2) used in Examples 1 and 2 were used as the primer.

```
Primer (1):
5'-GGGCATGGGTCAGAAGGATT-3'    (SEQ ID NO: 1)

Primer (2):
5'-CCTCGTCGCCCACATAG-3'       (SEQ ID NO: 2)
```

<Surfactant>

The following 9 types of substances were used as a surfactant, and experiment was carried out.

Level 1: TWEEN® 40

TWEEN® 40 is polyoxyethylene(20) sorbitan monopalmitate, and is a polyoxyethylene sorbitan fatty acid ester-based non-ionic surfactant. More particularly, TWEEN® 40 is polyoxyethylene sorbitan fatty acid monoester. TWEEN® 40 has HLB of 15.6, and is represented by the following formula. TWEEN® 40 was purchased from Wako Pure Chemical Industries, Ltd.

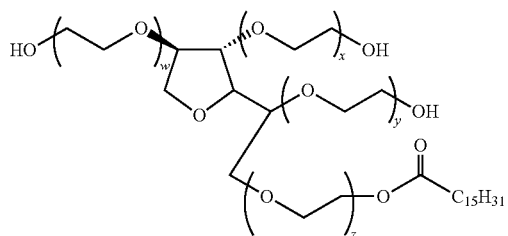

$w + x + y + z = 20$

Level 2: TWEEN® 60

TWEEN® 60 is polyoxyethylene(20) sorbitan monostearate, and is a polyoxyethylene sorbitan fatty acid ester-based non-ionic surfactant. More particularly, TWEEN® 60 is polyoxyethylene sorbitan fatty acid monoester. TWEEN® 60 has HLB of 15.0, and is represented by the following formula. TWEEN® 60 was purchased from Wako Pure Chemical Industries, Ltd.

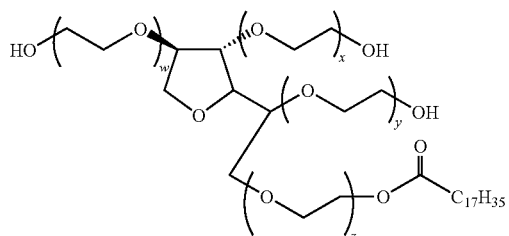

$w + x + y + z = 20$

Level 3: TWEEN® 80

TWEEN® 80 is polyoxyethylene(20) sorbitan monooleate, and is a polyoxyethylene sorbitan fatty acid ester-based non-ionic surfactant. More particularly, TWEEN® 80 is polyoxyethylene sorbitan fatty acid monoester. TWEEN® 80 has HLB of 14.9, and is represented by the following formula. TWEEN® 80 was purchased from Wako Pure Chemical Industries, Ltd.

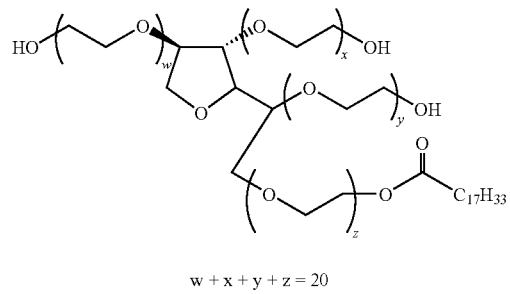

$w + x + y + z = 20$

Level 4: BRIJ® 35

BRIJ® 35 is polyoxyethylene(23) lauryl ether, and is a polyoxyethylene alkyl ether-based non-ionic surfactant. BRIJ® 35 has HLB of 16.9, and is represented by the following formula. BRIJ® 35 was purchased from Sigma.

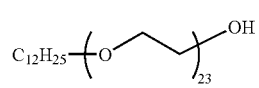

Level 5: BRIJ® 56

BRIJ® 56 is polyoxyethylene(10) cetyl ether, and is a polyoxyethylene alkyl ether-based non-ionic surfactant. BRIJ® 56 has HLB of 12.9, and is represented by the following formula. BRIJ® 56 was purchased from Sigma.

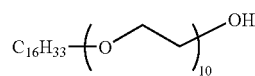

Level 6: BRIJ® 700

BRIJ® 700 is polyoxyethylene(100) stearyl ether, and is a polyoxyethylene alkyl ether-based non-ionic surfactant. BRIJ® 700 has HLB of 18.8, and is represented by the following formula. BRIJ® 700 was purchased from Sigma.

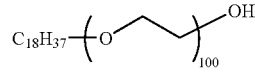

Level 7: TRITONS X-100

TRITON® X-100 is polyoxyethylene octylphenolether, and is a polyoxyethylene alkylphenolether-based non-ionic surfactant. TRITON® X-100 has HLB of 13.5, and is represented by the following formula. TRITON® X-100 was purchased from Wako Pure Chemical Industries, Ltd.

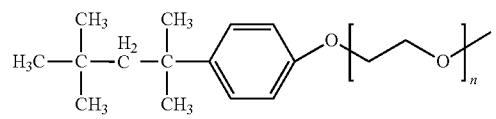

$n = 1 \sim 15$ (average = 9.5)

Level 8: TWEEN® 85

TWEEN® 85 is polyoxyethylene(20) sorbitan trioleate, and is a polyoxyethylene sorbitan fatty acid ester-based non-ionic surfactant. More particularly, TWEEN® 85 is polyoxyethylene sorbitan fatty acid triester. TWEEN® 85 has HLB of 11.0, and is represented by the following formula. TWEEN® 85 was purchased from Wako Pure Chemical Industries, Ltd.

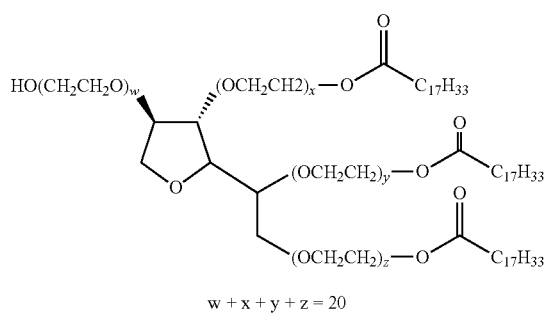

$w + x + y + z = 20$

Level 9: SPAN® 20

SPAN® 20 is sorbitan monolaurate, and is a sorbitan fatty acid ester-based non-ionic surfactant. SPAN® 20 has HLB of 8.6, and is represented by the following formula. SPAN® 20 was purchased from Wako Pure Chemical Industries, Ltd.

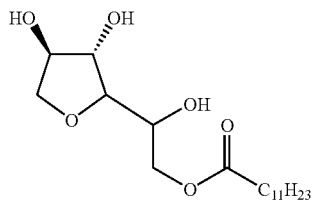

(2) Nucleic Acid Amplification Reaction

The amplification reaction was performed with the composition of a reaction solution shown below at 60° C. for 60 minutes. Bst. polymerase (NEB (New England Biolabs)) was used as an enzyme.

<Composition of Reaction Solution>

| | |
|---|---|
| 10 × Bst Buffer (Detergent Free) | 2.5 μL |
| 100 mM MgSO4 | 1.5 μL |
| 10% (v/v) surfactant | 0.25 μL |
| 100% DMSO | 1.25 μL |
| 25 mM dNTP each | 1.4 μL |
| SYBR® Green · (2000 times) | 0.5 μL |
| 50 μM primer (1) | 1.6 μL |
| 50 μM primer (2) | 1.6 μL |
| Bst. Polymerase | 1.0 μL |
| Nucleic acid fragment specimen obtained in (1), or purified water | 1.0 μL |
| Purified water | 12.4 μL |
| | 25.0 μL |

In each Level, 3 samples containing nucleic acid specimen, and 3 samples containing purified water in place of nucleic acid specimen (negative control) were prepared.

(3) Detection of Amplified Product

The amplification reaction in (2) above was carried out using a real-time fluorescence detection apparatus (MX3000P®, produced by Stratagene), and the fluorescent intensity was measured with time to detect the amplification. FIGS. 11 to 19 show the results. On the right of the figures, the time (Ct value, minutes) when an amount of fluorescence had reached 250 in the above graph was shown.

In Level 1 to Level 7 where a surfactant having HLB of 12 or more was used, amplification was detected only in a sample containing nucleic acid specimen. Namely, the presence of nucleic acid specimen can be detected by this amplification method.

In Level 8 and Level 9 where a surfactant having HLB of less than 12 was used, amplification was detected also in a sample containing no nucleic acid specimen (negative control). When the Ct values were compared, there was difference between the sample containing nucleic acid specimen and the sample containing no nucleic acid specimen.

From the above, the effect of a surfactant was demonstrated in this amplification method, and various surfactants can be used, and especially a surfactant having HLB of 12 or more can show high performance.

The effect of a surfactant is shown in Table 1, when amplification was carried out using Primer (1) and Primer (2).

If amplification is not detected in a sample containing no nucleic acid specimen (negative control) within 20 minutes from the mean value of time necessary for detection of amplification in a sample containing nucleic acid specimen, it was regarded that there is no problem in detection of nucleic acid specimen. If this is satisfied, the effect of the surfactant was evaluated as "◯".

If amplification is detected in a sample containing no nucleic acid specimen (negative control) within 20 minutes from the mean value of time necessary for detection of amplification in a sample containing nucleic acid specimen, but rapid amplification does not occur within 5 minutes, it was considered that detection of nucleic acid specimen is possible barely. If this is satisfied, the effect of the surfactant was evaluated as "Δ".

If amplification is detected in a sample containing no nucleic acid specimen (negative control) within 5 minutes from the mean value of time necessary for detection of amplification in a sample containing nucleic acid specimen, it was considered that detection of nucleic acid specimen is difficult. If this is satisfied, the effect of the surfactant was evaluated as "X".

TABLE 1

| Type of surfactant | HLB | Effect |
|---|---|---|
| BRIJ ® 700 | 18.8 | ◯ |
| BRIJ ® 35 | 16.9 | ◯ |
| TWEEN ® 20 | 16.7 | ◯ |
| TWEEN ® 40 | 15.6 | ◯ |
| TWEEN ® 60 | 15.0 | ◯ |
| TWEEN ® 80 | 14.9 | ◯ |
| TRITON ® X-100 | 13.5 | ◯ |
| BRIJ ® 56 | 12.9 | ◯ |
| TWEEN ® 85 | 11.0 | Δ |
| SPAN ® 20 | 8.6 | Δ |
| No surfactant | — | X |

◯: Detection is possible
Δ: Detection is possible, but difference from negative control is insufficient.
X: Detection is not possible.

Example 4

Effect (2) of Type of the Surfactant

Change of Primer (1) Preparation of Nucleic Acid Specimen Solution Containing Target Nucleic Acid Fragment 7.5 ng of HumanGenomic DNA (produced by Clontech) was heated at 98° C. for 3 minutes, and then a specific sequence in the target nucleic acid was amplified under the following conditions. As a negative control, a sample was also prepared by heating water under the same conditions.
<Primers>
Primers (3) and (4) used in Examples 1 and 2 were used as the primer.

```
Primer (3):
5'-CTTGCTGGCACCCAATA-3'      (SEQ ID NO: 3)

Primer (4):
5'-CCGGCGCATGGCTT-3'         (SEQ ID NO: 4)
```

<Surfactant>
The 9 types of substances used in Example 3 were used as a surfactant, and experiment was carried out.
(2) Nucleic Acid Amplification Reaction
The amplification reaction was performed with the composition of a reaction solution shown below at 60° C. for 60 minutes. Bst. polymerase (NEB (New England Biolabs)) was used as an enzyme.
<Composition of Reaction Solution>

| | |
|---|---|
| 10 × Bst Buffer (Detergent Free) | 2.5 µL |
| 100 mM MgSO4 | 1.5 µL |
| 10% (v/v) surfactant | 0.25 µL |
| 100% DMSO | 1.25 µL |
| 25 mM dNTP each | 1.4 µL |
| SYBR ® Green · (2000 times) | 0.5 µL |
| 50 µM primer (3) | 1.6 µL |
| 50 µM primer (4) | 1.6 µL |
| Bst. Polymerase | 1.0 µL |
| Nucleic acid fragment specimen obtained in (1), or purified water | 1.0 µL |
| Purified water | 12.4 µL |
| | 25.0 µL |

In each Level, 3 samples containing nucleic acid specimen, and 3 samples containing purified water in place of nucleic acid specimen (negative control) were prepared.
(3) Detection of Amplified Product
The amplification reaction in (2) above was carried out using a real-time fluorescence detection apparatus (MX3000P®, produced by Stratagene), and the fluorescent intensity was measured with time to detect the amplification. FIGS. 20 to 28 show the results. On the right of the figures, the time (Ct value, minutes) when an amount of fluorescence had reached 250 in the above graph was shown.
In Level 1 to Level 7 where a surfactant having HLB of 12 or more was used, amplification was detected only in a sample containing nucleic acid specimen, or amplification in a sample containing no nucleic acid specimen (negative control) was significantly slow. Namely, the presence of nucleic acid specimen can be detected by this amplification method.
In Level 8 and Level 9 where a surfactant having HLB of less than 12 was used, amplification was detected also in a sample containing no nucleic acid specimen (negative control). When the Ct values were compared, there was difference between the sample containing nucleic acid specimen and the sample containing no nucleic acid specimen.
From the above, various surfactants can be used in this amplification method, and especially a surfactant having HLB of 12 or more can show high performance.
The effect of a surfactant is shown in Table 2, when amplification was carried out using Primer (3) and Primer (4).
If amplification is not detected in a sample containing no nucleic acid specimen (negative control) within 20 minutes from the mean value of time necessary for detection of amplification in a sample containing nucleic acid specimen, it was regarded that there is no problem in detection of nucleic acid specimen. If this is satisfied, the effect of the surfactant was evaluated as "○".
If amplification is detected in a sample containing no nucleic acid specimen (negative control) within 20 minutes from the mean value of time necessary for detection of amplification in a sample containing nucleic acid specimen, but rapid amplification does not occur within 5 minutes, it was considered that detection of nucleic acid specimen is possible barely. If this is satisfied, the effect of the surfactant was evaluated as "Δ".
If amplification is detected in a sample containing no nucleic acid specimen (negative control) within 5 minutes from the mean value of time necessary for detection of amplification in a sample containing nucleic acid specimen, it was considered that detection of nucleic acid specimen is difficult. If this is satisfied, the effect of the surfactant was evaluated as "X".

TABLE 2

| Type of surfactant | HLB | Effect |
|---|---|---|
| BRIJ ® 700 | 18.8 | ○ |
| BRIJ ® 35 | 16.9 | ○ |
| TWEEN ® 20 | 16.7 | ○ |
| TWEEN ® 40 | 15.6 | ○ |
| TWEEN ® 60 | 15.0 | ○ |
| TWEEN ® 80 | 14.9 | ○ |
| TRITON ® X-100 | 13.5 | ○ |
| BRIJ ® 56 | 12.9 | ○ |
| TWEEN ® 85 | 11.0 | X |
| SPAN ® 20 | 8.6 | Δ |
| No surfactant | — | X |

○: Detection is possible
Δ: Detection is possible, but difference from negative control is insufficient.
X: Detection is not possible.

From the fact that a result which is same as that of Example 3 was obtained, it was confirmed that the effect of a surfactant does not depend on the primer, but is a universal effect.

Example 5

Nucleic Acid Amplification Using BCABEST™ Polymerase (1) Preparation of Nucleic Acid Specimen Solution Containing Target Nucleic Acid Fragment
7.5 ng of HumanGenomic DNA (produced by Clontech) was heated at 98° C. for 3 minutes and then a specific sequence in the target nucleic acid was amplified under the following conditions. As a negative control, a sample was also prepared by heating water under the same conditions.
<Primers>
Primers (1) and (2) used in Example 1 were used as the primer.

```
Primer (1):
5'-GGGCATGGGTCAGAAGGATT-3'    (SEQ ID NO: 1)

Primer (2):
5'-CCTCGTCGCCCACATAG-3'       (SEQ ID NO: 2)
```

<Surfactant>
TWEEN® 20 (Wako Pure Chemical Industries, Ltd.) was used as a surfactant.

(2) Nucleic Acid Amplification Reaction

The amplification reaction was performed with the composition of a reaction solution shown below at 60° C. for 60 minutes. BCABEST™ DNA polymerase (TaKaRa) was used as an enzyme.

<Composition of Reaction Solution>

| | |
|---|---|
| 10 × Bst Buffer (Detergent Free) | 2.5 μL |
| 100 mM MgSO4 | 1.5 μL |
| 10% (v/v) TWEEN ® 20 | 0.25 μL |
| 100% DMSO | 1.25 μL |
| 25 mM dNTP each | 1.4 μL |
| SYBR ® Green · (2000 times) | 0.5 μL |
| 50 μM primer (1) | 1.6 μL |
| 50 μM primer (2) | 1.6 μL |
| BCABEST ™ DNA polymerase | 1.0 μL |
| Nucleic acid fragment specimen obtained in (1), or purified water | 1.0 μL |
| Purified water | 12.4 μL |
| | 25.0 μL |

In each Level, 2 samples containing nucleic acid specimen, and 2 samples containing purified water in place of nucleic acid specimen (negative control) were prepared.

Figure 29:
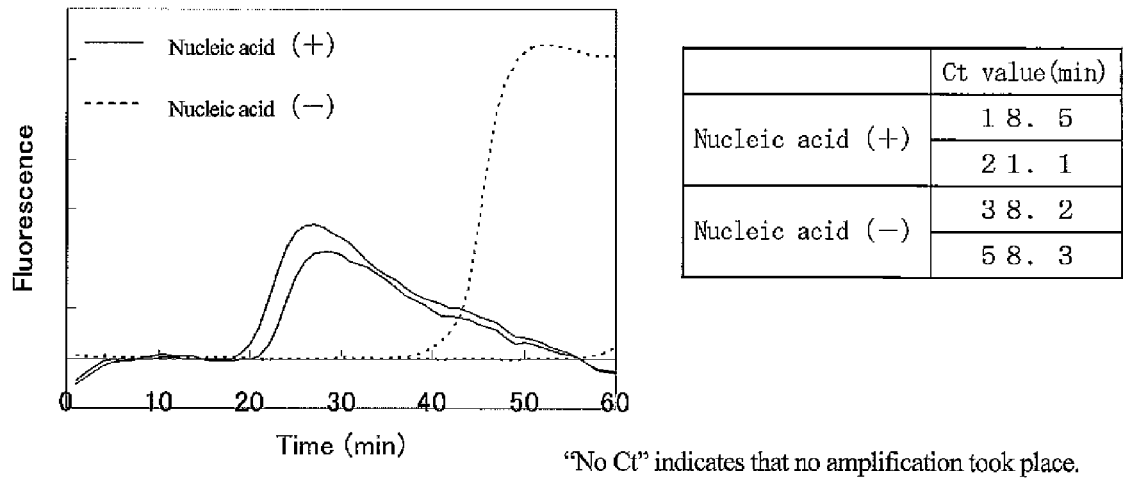
FIG. 29 shows the results of detecting amplified products of Level 1 (surfactant (−)) in Example 5.
Figure 30:
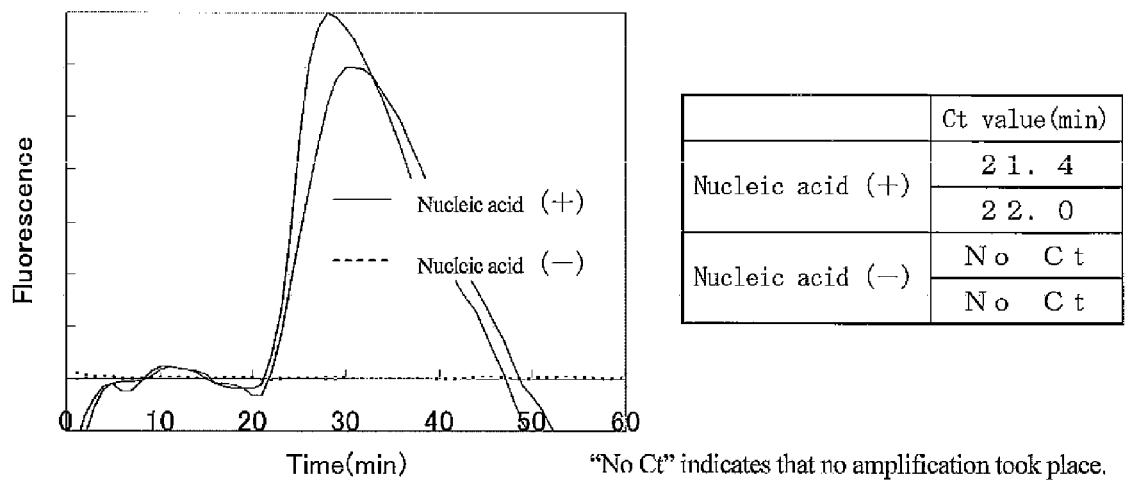
FIG. 30 shows the results of detecting amplified products of Level 1 (surfactant (+)) in Example 5.

The following surfactant was used for the experiment.
Level 1: No Surfactant
Level 2: With Surfactant (TWEEN® 20)
(3) Detection of Amplified Product The amplification reaction in (2) above was carried out using a real-time fluorescence detection apparatus (MX3000P®, produced by Stratagene), and the fluorescent intensity was measured with time to detect the amplification. FIGS. 29 and 30 show the results. On the right of the figures, the time (Ct value, minutes) when an amount of fluorescence had reached 250 in the above graph was shown.

In Level 1 where surfactant was not added, amplification was detected also in samples which contain no nucleic acid specimen (negative control). Namely, the presence of nucleic acid specimen can not be detected by this amplification method.

In Level 2 where surfactant was added, amplification was detected only in samples which contains nucleic acid specimen. Namely, the presence of nucleic acid specimen can be detected by this amplification method.

These results are the same as those where Bst. Polymerase was used as a polymerase. Namely, it was confirmed that the effect of a surfactant does not depend on the type of the strand-displacement-type polymerase, but is a universal effect.

Example 6

Detection of Single Nucleotide Mutation (1) Preparation of Nucleic Acid Specimen Solution Containing Target Nucleic Acid Fragment 7.5 ng of human genome of gene type of β 2AR46(A) and human genome of gene type of β 2AR46(G) were respectively heated at 98° C. for 3 minutes and then a specific sequence in the target nucleic acid was amplified under the following conditions. As a negative control, a sample was also prepared by heating water under the same conditions.

The human genome of gene type of β 2AR46(G) is obtained by mutation of single nucleotide in the genome of gene type of β 2AR46(A).

<Primers>

Primers (3) and (4) used in Examples 1 and 4 were used as the primer.

```
Primer (3):
5'-CTTGCTGGCACCCAATA-3'        (SEQ ID NO: 3)

Primer(4):
5'-CCGGCGCATGGCTT-3'           (SEQ ID NO: 4)
```

This primer set is completely complementary to the human genome of gene type of β 2AR46(A).
(2) Nucleic Acid Amplification Reaction The amplification reaction was performed with the composition of a reaction solution shown below at 60° C. for 60 minutes. Bst. polymerase (NEB (New England Biolabs)) was used as an enzyme.

<Composition of Reaction Solution>

| | |
|---|---|
| 10 × Bst Buffer (Detergent Free) | 2.5 μL |
| 100 mM MgSO4 | 1.5 μL |
| 10% (v/v) TWEEN ® 20 | 0.25 μL |
| 100% DMSO | 1.25 μL |
| 25 mM dNTP each | 1.4 μL |
| SYBR ® Green I (2000 times) | 0.5 μL |
| 50. M Primer (3) | 1.6 μL |
| 50. M Primer (4) | 1.6 μL |
| Bst. Polymerase | 1.0 μL |
| Nucleic acid fragment specimen obtained in (1), or purified water | 1.0 μL |
| Purified water | 12.4 μL |
| | 25.0 μL |

Figure 31:
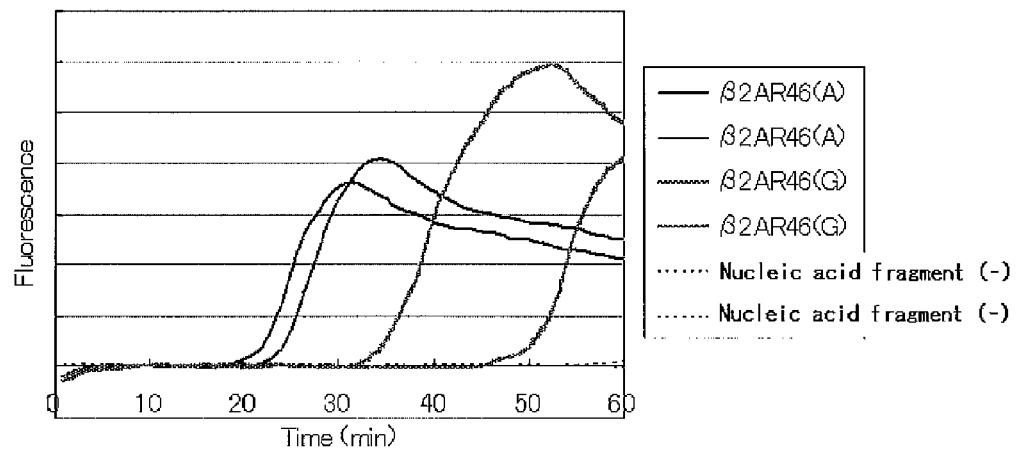
FIG. 31 shows the results of detecting amplified products in Example 6.

In each Level, 2 samples containing nucleic acid specimen, and 2 samples containing purified water in place of nucleic acid specimen (negative control) were prepared.
(3) Detection of Amplified Product The amplification reaction in (2) above was carried out using a real-time fluorescence detection apparatus (MX3000P®, produced by Stratagene), and the fluorescent intensity was measured with time to detect the amplification. FIG. 31 shows the results.

The amplification rates in the sample containing human genome of gene type of β 2AR46(A) were higher than those in the sample containing human genome of gene type of β 2AR46(G). By observing the difference of amplification rate, a mutation of single nucleotide in human genome can be identified by using this amplification method. Amplification was not detected in the sample containing no nucleic acid specimen (negative control).

The time (Ct value) when an amount of fluorescence had reached 250 in the above graph was calculated by using the analysis software of MX3000P®. The results are shown in Table 3.

TABLE 3

| | Ct value (minute) |
|---|---|
| β 2AR46(A) | 19.8 |
| | 22.7 |
| β 2AR46(G) | 32.9 |
| | 47.0 |
| No nucleic acid specimen | No Ct |
| | No Ct |

※ "No Ct" indicates that no amplification took place.

It is understood that the amplification rates in the sample of gene type of β 2AR46(A) are higher than those in the sample of gene type of β 2AR46(G).

Example 7

Speeding-Up of Detection (1) Preparation of Nucleic Acid Specimen Solution Containing Target Nucleic Acid Fragment 37.5 ng of HumanGenomic DNA (produced by Clontech) was heated at 98° C. for 3 minutes and then a specific sequence in the target nucleic acid was amplified under the following conditions.
<Primers>

Primers (1) and (2) used in Example 1 were used as the primer.

```
Primer (1):
5'-GGGCATGGGTCAGAAGGATT-3'      (SEQ ID NO: 1)

Primer (2):
5'-CCTCGTCGCCCACATAG-3'         (SEQ ID NO: 2)
```

<Surfactant>
TWEEN® 20 was used as a surfactant.
(2) Nucleic Acid Amplification Reaction The amplification reaction was performed with the composition of a reaction solution shown below at 60° C. for 60 minutes. BCABEST™ DNA polymerase (TaKaRa) was used as an enzyme.

| | |
|---|---|
| 10 × Bst Buffer (Detergent Free) | 2.5 μL |
| 100 mM MgSO4 | 1.5 μL |
| 10% (v/v) TWEEN ® 20 | 0.25 μL |
| 100% DMSO | 1.25 μL |
| 25 mM dNTP each | 1.4 μL |
| SYBR ® Green · (2000 times) | 0.5 μL |
| 50 μM primer (1) | 1.6 μL |
| 50 μM primer (2) | 1.6 μL |
| BCABEST ™ DNA polymerase | 1.0 μL |
| Nucleic acid fragment specimen obtained in (1), or purified water | 1.0 μL |
| Purified water | 12.4 μL |
| | 25.0 μL |

Figure 32:
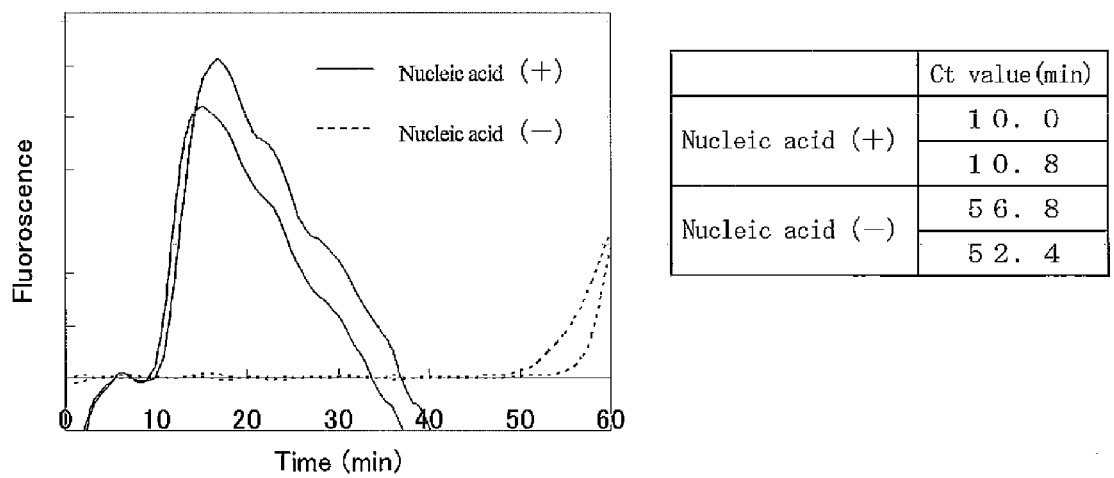
FIG. 32 shows the results of detecting amplified products in Example 7.

In each Level, 2 samples containing nucleic acid specimen, and 2 samples containing purified water in place of nucleic acid specimen (negative control) were prepared.
(3) Detection of Amplified Product The amplification reaction in (2) above was carried out using a real-time fluorescence detection apparatus (MX3000P®, produced by Stratagene), and the fluorescent intensity was measured with time to detect the amplification. FIG. 32 shows the results. On the right of the figure, the time (Ct value, minutes) when an amount of fluorescence had reached 250 in the above graph was shown.

Detection of the target gene was succeeded within 10 minutes by performing the amplification reaction under the conditions described in this example.

Example 8

Nucleic Acid Amplification Reaction Using 3 Types of Primers (1) Preparation of Nucleic Acid Specimen Solution Containing Target Nucleic Acid Fragment 3.0 ng of HumanGenomic DNA (produced by Clontech), was heated at 98° C. for 3 minutes to be single-stranded, and a sequence in a β-actin gene was then amplified under the following conditions. As a negative control, a sample was also prepared by heating water under the same above conditions.
<Primers>

Primers were designed using the β-actin gene as a target. Each primer sequence is as shown below.

```
Primer (1) (Forward 1):
5'-GGGCATGGGTCAGAAGGATT-3'       (SEQ ID NO: 1)

Primer (2) (Reverse 1):
5'-CCTCGTCGCCCACATAG-3'          (SEQ ID NO: 2)

Primer (3) (Reverse 2):
5'-GATGGGGTACTTCAGGGT-3'         (SEQ ID NO: 6)
```

(2) Nucleic Acid Amplification Reaction

The amplification reaction was performed with the composition of a reaction solution shown below at 60° C. for 60 minutes. Bst. DNA polymerase (NEB (New England Biolabs)) was used as an enzyme.

<Composition of Reaction Solution>

| | |
|---|---|
| 10 × Bst Buffer (DF) | 2.5 μL |
| 100 mM MgSO4 | 1.5 μL |
| 10% (v/v) TWEEN ® 20 | 0.25 μL |
| 100% DMSO | 1.25 μL |
| 25 mM dNTP each | 1.4 μL |
| SYBR ® Green · (2000 times) | 0.5 μL |
| 50 μM primer (1) | 1.8 μL |
| 50 μM primer (2) | 1.8 μL |
| 50 μM primer (3) | 1.8 μL |
| Bst. Polymerase | 1.0 μL |
| Nucleic acid fragment specimen solution obtained in (1) (3.0 ng) | 1.0 μL |
| Purified water | 10.2 μL |
| | 25.0 μL |

Figure 33:
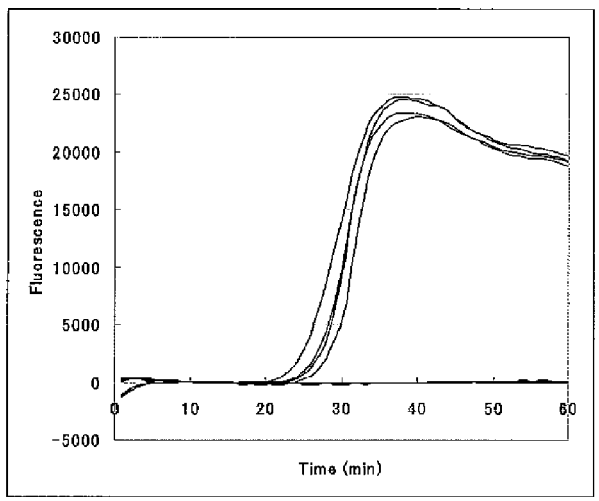
FIG. 33 shows the results of detecting amplified products in Example 8.

In the case of the negative control, water was added instead of the nucleic acid fragment specimen solution.
(3) Detection of Amplified Product The amplification reaction in (2) above was carried out using a real-time fluorescence detection apparatus (MX3000P, produced by Stratagene), and the fluorescent intensity was measured with time to detect the amplification. FIG. 33 shows the results.

It was found that amplification took place only in the case of samples derived from the nucleic acid specimen. Specifically, nonspecific amplification did not take place in the case of water. Here, the time (Ct value) when an amount of fluorescence had reached 250 in the above graph was calculated using MX3000P analysis software. Table 4 shows the results.

TABLE 4

| Template | Ct (Th 250) |
|---|---|
| Genome | 26.6 |
| | 25.4 |
| | 25.9 |
| | 24.8 |
| Water | No Ct |
| | No Ct |
| | No Ct |
| | No Ct |

※ "No Ct" indicates that no amplification took place.

Example 9

Method of Amplifying Nucleic Acid Using 4 Primers (1) Preparation of Nucleic Acid Specimen Solution Containing Target Nucleic Acid Fragment 3.0 ng of HumanGenomic DNA (produced by Clontech), was heated at 98° C. for 3 minutes to be single-stranded, and a sequence in a β-actin gene was then amplified under the following conditions. As a negative control, a sample was also prepared by heating water under the same above conditions.

<Primers>

Primers were designed using the β-actin gene as a target. Each primer sequence is as shown below.

```
Primer (1) (Forward 1):
5'-GGGCATGGGTCAGAAGGATT-3'        (SEQ ID NO: 1)

Primer (2) (Reverse 1):
5'-CCTCGTCGCCCACATAG-3'           (SEQ ID NO: 2)

Primer (3) (Reverse 2):
5'-GATGGGGTACTTCAGGGT-3'          (SEQ ID NO: 6)

Primer (4) (Forward 2):
5'-TGTCCTTTCCTTCCCAG-3'           (SEQ ID NO: 7)
```

(2) Nucleic Acid Amplification Reaction

The amplification reaction was performed with the composition of a reaction solution shown below at 60° C. for 60 minutes. Bst. DNA polymerase (NEB (New England Biolabs)) was used as an enzyme.

<Composition of Reaction Solution>

| | |
|---|---|
| 10 × Bst Buffer (DF) | 2.5 µL |
| 100 mM MgSO4 | 1.5 µL |
| 10% (v/v) TWEEN ® 20 | 0.25 µL |
| 100% DMSO | 1.25 µL |
| 25 mM dNTP each | 1.4 µL |
| SYBR ® Green · (2000 times) | 0.5 µL |
| 50 µM primer (1) | 1.8 µL |
| 50 µM primer (2) | 1.8 µL |
| 50 µM primer (3) | 1.8 µL |
| 50 µM primer (4) | 1.8 µL |
| Bst. Polymerase | 1.0 µL |
| Nucleic acid fragment specimen solution obtained in (1) (3.0 ng) | 1.0 µL |
| Purified water | 8.4 µL |
| | 25.0 µL |

In the case of the negative control, water was added instead of the nucleic acid fragment specimen solution.

(3) Detection of Amplified Product

Figure 34:
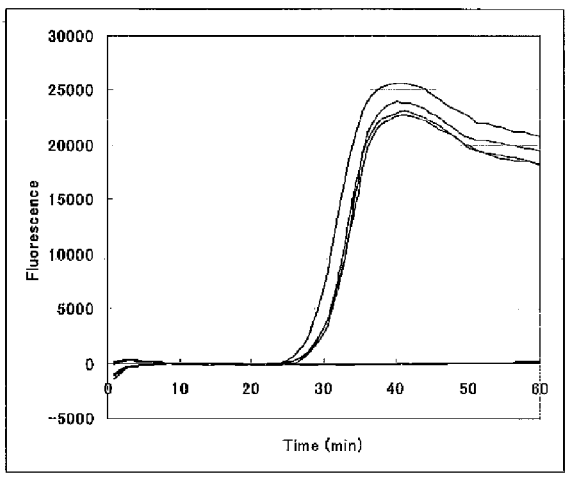
FIG. 34 shows the results of detecting amplified products in Example 9.

The amplification reaction in (2) above was carried out using a real-time fluorescence detection apparatus (MX3000P®, produced by Stratagene), and the fluorescent intensity was measured with time to detect the amplification. FIG. 34 shows the results.

It was found that amplification took place only in the case of samples derived from the nucleic acid specimen. Specifically, nonspecific amplification did not take place in the case of water. Here, the time (Ct value) when an amount of fluorescence had reached 250 in the above graph was calculated using MX3000P® analysis software. Table 5 shows the results.

TABLE 5

| Template | Ct (Th 250) |
|---|---|
| Genome | 23.9 |
| | 24.9 |
| | 23.5 |
| | 21.4 |
| Water | No Ct |
| | No Ct |
| | No Ct |
| | No Ct |

※ "No Ct" indicates that no amplification took place.

---

The invention claimed is:

1. A nucleic acid amplification method which comprises performing isothermal incubation of a reaction solution wherein said reaction solution comprising
at least one type of deoxynucleotide triphosphate,
a DNA polymerase having a strand displacement activity,
a divalent cation,
at least 0.01% or more surfactant,
at least two types of oligonucleotide primers, each not having a structure which forms a loop structure, wherein a 5' terminal region is complementary to the region, which is elongated from a 3' terminal region of the primer, and
a nucleic acid fragment as a template, and
said reaction solution is free of any primers having a structure which forms a loop structure,
so as to perform a polymerase reaction that initiates from the 3' end of the primers and thus amplifying the nucleic acid fragment wherein, (i) (a) one of said at least two types of oligonucleotide primers is annealed to a template nucleic acid strand of the nucleic acid fragment, and a synthesis reaction is initiated from the 3' end of said annealed oligonucleotide primer due to the action of the DNA polymerase so as to synthesize a primer elongation product; (b) one or more oligonucleotide primers other than the oligonucleotide primer of step (a) are caused to enter the double-stranded nucleic acid obtained in step (a) without performing any denaturation of the double-stranded nucleic acid via application of a temperature higher than that in step (a), and then, a synthesis reaction is initiated from the 3' ends of said one or more oligonucleotide primers by the action of the DNA polymerase so as to synthesize further primer elongation products; (c) the primer of step (a) is annealed again to the nucleic acid liberated in step (b) and a synthesis reaction is then initiated from the 3' end of said primer by the action of the DNA polymerase, so as to synthesize further primer elongation products; and (d) the double-stranded nucleic acid obtained in step (b) is used again as a template in step (b); or (ii) (a) one of said at least two types of primers is annealed to a template nucleic acid strand of the nucleic acid fragment, and a synthesis reaction is initiated from the 3' end of said annealed oligonucleotide primer due to the action of the DNA polymerase so as to synthesize a primer elongation product; (b) the oligonucleotide primer of step (a) is caused to enter the double-stranded nucleic acid obtained in step (a) without performing any denaturation of the double-stranded nucleic acid via application of a temperature higher than that in step (a), and then, a synthesis reaction is initiated from the 3' end of said oligonucleotide primer by the action of the DNA polymerase so as to synthesize a primer elongation product; (c) one or more oligonucleotide primers other than the primer of step (a) are annealed to the nucleic acid liberated in step (b) and a synthesis reaction is then initiated from the 3' ends of said one or more oligonucleotide primers by the action of the DNA polymerase, so as to synthesize further primer elongation products; and (d) the double-stranded nucleic acid obtained in step (b) is used again as a template in step (b).

2. The method of claim 1 wherein the reaction solution contains at least 0.05% or more surfactant.

3. The method of claim 1 wherein the surfactant is a nonionic surfactant.

4. The method of claim 3 wherein the HLB value of the nonionic surfactant is 12 or more.

5. The method of claim 4 wherein the HLB value of the nonionic surfactant is 14 or more.

6. The method of claim 3 wherein the nonionic surfactant is selected from the group consisting of a polyoxyethylene sorbitan fatty acid ester-based surfactant, and a polyoxyethylene alkyl ether-based surfactant.

7. The method of claim 6 wherein the polyoxyethylene sorbitan fatty acid ester-based surfactant is a polyoxyethylene sorbitan mono fatty acid ester.

8. The method of claim 7 wherein the polyoxyethylene sorbitan mono fatty acid ester is represented by the following formula:

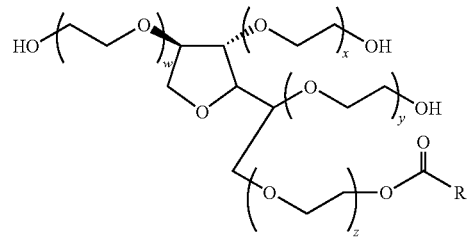

wherein x+y+z+w=20, and R is an alkyl group having a carbon number of 12 to 18.

9. The method of claim 6 wherein the polyoxyethylene sorbitan fatty acid ester-based surfactant is at least one which is selected from the group consisting of polyoxyethylene(20) sorbitane monolaurate, polyoxyethylene(20) sorbitan monopalmitate, polyoxyethylene(20)sorbitan monostearate, and polyoxyethylene(20)sorbitan monooleate.

10. The method of claim 1 wherein the reaction solution further contains a melting temperature adjusting agent.

11. The method of claim 10 wherein the melting temperature adjusting agent is dimethyl sulfoxide, betaine, formamide, or glycerol, or a mixture of two or more types thereof.

12. The method of claim 1 wherein the reaction solution contains each deoxynucleotide triphosphate of 0.1 to 3.0 mM.

13. The method of claim 1 wherein the reaction solution contains 1 µM to 50 µM of the oligonucleotide primers.

14. The method of claim 1 wherein the oligonucleotide primers are complementary to portions of the template nucleic acid fragment.

15. The method of claim 1 wherein only the 3' terminal regions of the oligonucleotide primers are complementary to portions of the template nucleic acid fragment.

16. The method of claim 1 wherein the oligonucleotide primers are complementary to only consecutive 1 site of the template nucleic acid fragment.

17. The method of claim 1 wherein regions of the template, to which the at least two types of oligonucleotide primers are annealed, are positioned within a region of 1000 bp or less of the template.

18. The method of claim 1 wherein the DNA polymerase having a strand displacement activity is at least one polymerase selected from the group consisting of a Bacillus stearothermophilus-derived 5'→3' exonuclease-deficient DNA polymerase, a Bacillus caldotenax-derived 5'→3' exonuclease-deficient DNA polymerase, and a Thermococcus litoralis-derived 5'→3' exonuclease-deficient DNA polymerase.

19. The method of claim I wherein the reaction solution is incubated isothermally at a temperature of 50° C. to 100° C.

20. The method of claim 1 wherein the time for the isothermal incubation of the reaction solution is within 60 minutes.

21. The method of claim 1 wherein the reaction solution further contains one or more types of additional oligonucleotide primers.

22. The method of claim 21 wherein regions of the template, to which the at least two types of oligonucleotide primers and the one or more types of additional oligonucleotide primers are annealed, are positioned within a region of 1000 bp or less of the template.

23. A method for detecting the presence or the absence of a mutation in a target nucleic acid sequence, which comprises performing the nucleic acid amplification method of claim 1.

24. The method of claim 23 which comprises the following steps of:

(1) isothermally incubating a reaction solution comprising at least one type of deoxynucleotide triphosphate, at least one type of DNA polymerase having a strand displacement activity, a divalent cation, at least one type of nonionic surfactant, at least two types of oligonucleotide primers wherein one or more of the at least two types of oligonucleotide primers contains a mutation site and all the at least two types of oligonucleotide primers do not have a structure which forms a loop structure, wherein a 5' terminal region is complementary to the region, which is elongated from a 3' terminal region of the primer, and a nucleic acid fragment containing a target nucleic acid sequence as a template, wherein said reaction solution is free of any primers having a structure which forms a loop structure; and (2) determining the presence or the absence of a mutation based on a difference in amplification rates between a nucleic acid fragment having the mutation and a nucleic acid fragment not having the mutation, or based on whether or not a nucleic acid amplification reaction takes place by a polymerase reaction that is initiated from the 3' ends of the primers.

25. The method of claim 24 wherein the HLB value of the nonionic surfactant is 12 or more.

26. The method of claim 24 wherein the HLB value of the nonionic surfactant is 14 or more.

27. The method of claim 24 wherein the nonionic surfactant is selected from the group consisting of a polyoxyethylene sorbitan fatty acid ester-based surfactant, and a polyoxyethylene alkyl ether-based surfactant.

28. The method of claim 1 wherein only two or three types of oligonucleotide primers are contained in the reaction.

* * * * *

SEQUENCE LISTING

<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 1
gggcatgggt cagaaggatt                                              20

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 2
cctcgtcgcc cacatag                                                 17

```
<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 3
cttgctggca cccaata                                                     17

<210> SEQ ID NO 4
<211> LENGTH: 14
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 4
ccggcgcatg gctt                                                        14

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 5
gggcatgggt cagaaggatt cctatgtggg cgacgagg                              38

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 6
gatggggtac ttcagggt                                                    18

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 7
tgtcctttcc ttcccag                                                     17
```